United States Patent
Conroy et al.

(10) Patent No.: US 11,116,442 B1
(45) Date of Patent: Sep. 14, 2021

(54) IMAGE INTEGRITY AND REPEATABILITY SYSTEM

(71) Applicant: CAPTUREPROOF, Inc., San Francisco, CA (US)

(72) Inventors: Meghan Patricia Conroy, San Francisco, CA (US); Jaroslaw Walery Winniczek, Daly City, CA (US); David Chocron, Mill Valley, CA (US)

(73) Assignee: CAPTUREPROOF, INC., San Francisco, CA (US)

( * ) Notice: Subject to any disclaimer, the term of this patent is extended or adjusted under 35 U.S.C. 154(b) by 0 days.

(21) Appl. No.: 16/436,817

(22) Filed: Jun. 10, 2019

Related U.S. Application Data

(60) Provisional application No. 62/683,010, filed on Jun. 10, 2018.

(51) Int. Cl.
*A61B 5/00* (2006.01)
*G06T 7/90* (2017.01)
*G06T 7/00* (2017.01)

(52) U.S. Cl.
CPC ............ *A61B 5/442* (2013.01); *G06T 7/0012* (2013.01); *G06T 7/90* (2017.01); *G06T 2207/30088* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,752,441 | B2 * | 6/2014 | Asaoka | G01J 3/524 73/866 |
| 8,988,686 | B2 * | 3/2015 | Hillebrand | G01J 3/50 356/421 |
| 2010/0185064 | A1 * | 7/2010 | Bandic | A61B 5/415 600/306 |
| 2015/0206313 | A1 * | 7/2015 | Reif | G06F 3/017 382/103 |
| 2016/0284084 | A1 * | 9/2016 | Gurcan | G06T 7/0016 |
| 2017/0076142 | A1 * | 3/2017 | Chang | G06T 7/90 |
| 2017/0272741 | A1 * | 9/2017 | Maltz | G06K 7/1417 |

* cited by examiner

*Primary Examiner* — Omar S Ismail
(74) *Attorney, Agent, or Firm* — Robert Crownover

(57) ABSTRACT

A method and instructions for operating an image integrity and repeatability system can comprise: acquiring an original image; extracting a protocol from the original image; recording the original image to an image history; determining an area within an image frame of the original image as a skin area; creating a background as the inverse of the skin area within the image frame of the original image; and acquiring a subsequent image including: extracting an image parameter from the subsequent image, providing feedback based on the image parameter being outside a threshold, prohibiting capture of the subsequent image based on the image parameter being outside the threshold, displaying the background overlaid on the subsequent image, and storing the subsequent image to the image history based on the image parameter of the subsequent image being within the threshold.

10 Claims, 14 Drawing Sheets

IMAGE INTEGRITY AND REPEATABILITY SYSTEM

CROSS-REFERENCE TO RELATED APPLICATION(S)

This claims priority benefit to all common subject matter of U.S. Provisional Patent Application No. 62/683,010 filed Jun. 10, 2018. The content of this application, in its entirety, is incorporated herein by reference.

TECHNICAL FIELD

This disclosure relates to imaging technologies, more particularly to imaging technologies for improving image integrity and repeatability.

BACKGROUND

In recent times, imaging technology has advanced with a tremendous pace. The rapidly growing portable electronics market, e.g. cellular phones, tablet computers, and PDAs, are an integral facet of modern life and has made imaging technologies ubiquitous and readily available.

Together with the development and supply of imaging technology, a need to utilize this low cost readily available imaging technology for analysis, diagnostics, and comparison purposes has arisen. Many fields have discovered a need for clear, accurate, consistently arranged, and time variant images. These fields cover wide implementation areas including construction management, insurance, and medicine.

In one example, external visual imaging techniques have long been an integral part of diagnosing and treating patient ailments. Some medical arts such as plastic surgery rely almost exclusively on visual end points and imaging.

Illustratively, scars and their healing are often characterized through a doctor's visual analysis of the patient's skin. A doctor monitoring the healing of a scar is primarily concerned with the size, shape and visibility of the scar at a given time as well as how the size, shape, color, and visibility of the scar are changing over time. Being able to review close up images, in greater detail, of the subject or relevant area are of equal importance.

Further, in the cosmetics industry, research scientists must visually study how make-up, creams (e.g. wrinkle and cellulite treatments), and other products affect the appearance of subjects over a course of treatment.

Yet further, pharmaceutical researchers involved in clinical trials must visually study experimental topical therapeutics to determine the efficacy of such therapeutics on patients suffering from various skin ailments. The results of such visual studies are then used to support regulatory filings with the goal of having such therapeutics approved for sale to consumers.

Since external visual imaging in the medical arts is concerned with the appearance and presentation of how certain structures on the human body are visually changing over time, both still and motion photography are vital tools for image acquisition, storage and analysis. There is a clear need to produce clear, consistent, and repeatable photographs. However, the use of still and motion photography in the medical arts presents a unique set of challenges.

A primary challenge inherent in the use of still and motion photography is this inability to capture consistent images due to different unique lighting environments and image backgrounds. While a still or motion image may provide information, often the ability to truly see change and make diagnoses may require the ability to more closely view an image in greater detail. When patients send and/or share images with their practitioner or any other healthcare professional, they may lack the ability to ensure color consistency, which can be crucial in delivering effective diagnoses.

The common trait of these prior developments is the high level of training, skill, and work required to interface with the technology, manipulate images, and analyze regions of the images more closely. These prior developments in imaging are therefore expensive and time consuming to use.

Solutions have been long sought but prior developments have not taught or suggested any complete solutions, and solutions to these problems have long eluded those skilled in the art. Thus, there remains a considerable need for systems and methods that can provide fast, intuitive, consistent, and repeatable images.

SUMMARY

A method and instructions for operating an imaging system, providing significantly improved image integrity and repeatability, are disclosed. A method and instructions for operating an image integrity and repeatability system can comprise: acquiring an original image; extracting a protocol from the original image; recording the original image to an image history; determining an area within an image frame of the original image as a skin area; creating a background as the inverse of the skin area within the image frame of the original image; and acquiring a subsequent image including: extracting an image parameter from the subsequent image, providing feedback based on the image parameter being outside a threshold, prohibiting capture of the subsequent image based on the image parameter being outside the threshold, displaying the background overlaid on the subsequent image, and storing the subsequent image to the image history based on the image parameter of the subsequent image being within the threshold.

Other contemplated embodiments can include objects, features, aspects, and advantages in addition to or in place of those mentioned above. These objects, features, aspects, and advantages of the embodiments will become more apparent from the following detailed description, along with the accompanying drawings.

BRIEF DESCRIPTION OF THE DRAWINGS

The image system is illustrated in the figures of the accompanying drawings which are meant to be exemplary and not limiting, in which like reference numerals are intended to refer to like components, and in which.

DETAILED DESCRIPTION

Figure 1:
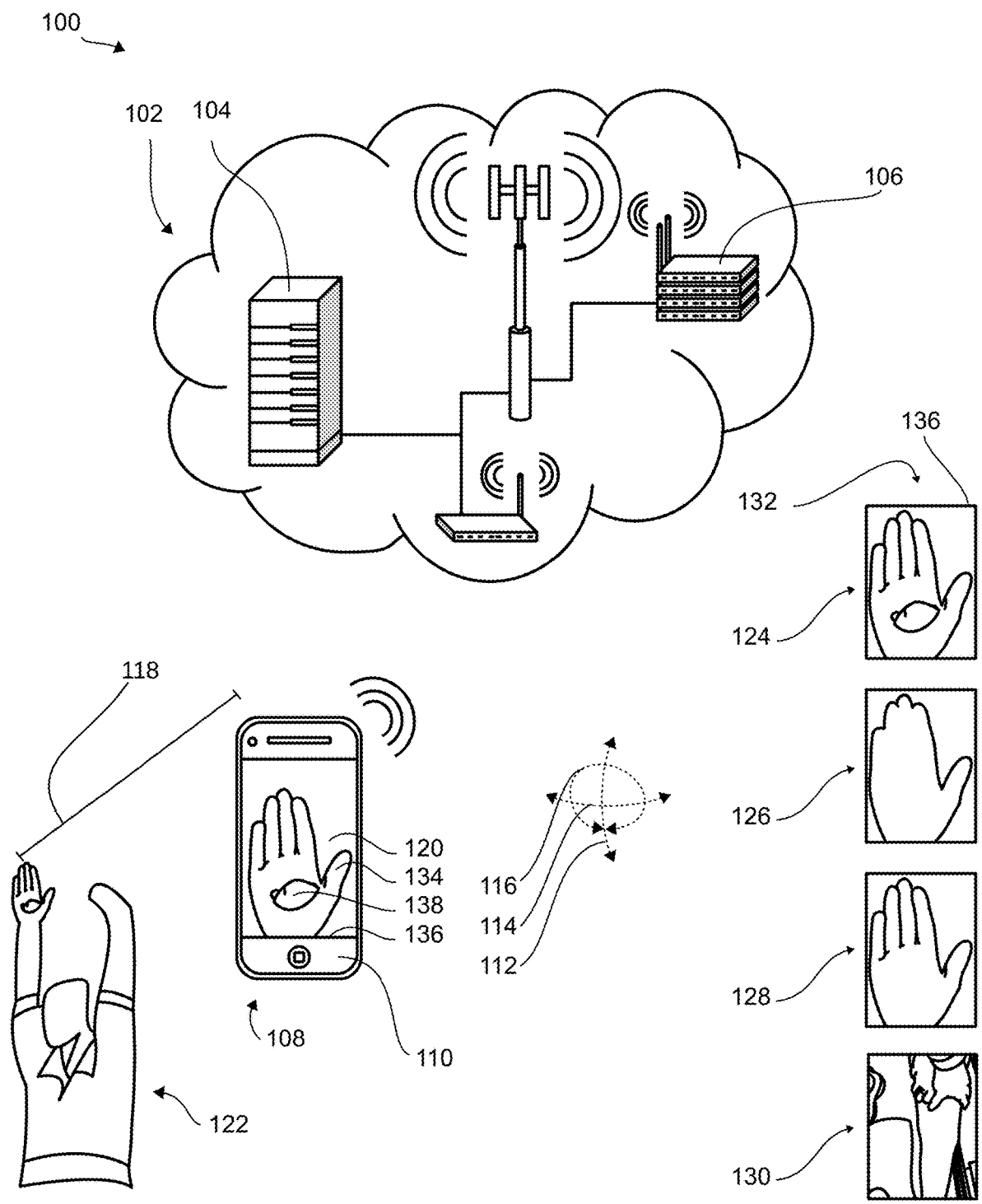
FIG. 1 is a block diagram of the image system.

In the following description, reference is made to the accompanying drawings that form a part hereof, and in which are shown by way of illustration, embodiments in which the image system may be practiced. It is to be understood that other embodiments may be utilized, and structural or procedural changes may be made without departing from the scope of the image system.

When features, aspects, or embodiments of the image system are described in terms of steps of a process, an operation, a control flow, or a flow chart, it is to be understood that the steps can be combined, performed in a different order, deleted, or include additional steps without departing from the image system as described herein.

The image system is described in sufficient detail to enable those skilled in the art to make and use the image system and provide numerous specific details to give a thorough understanding of the image system; however, it will be apparent that the image system may be practiced without these specific details.

In order to avoid obscuring the image system, some well-known system configurations, algorithms, methods, and descriptions are not disclosed in detail. Likewise, the drawings showing embodiments of the system are semi-diagrammatic and not to scale and, particularly, some of the dimensions are for the clarity of presentation and are shown greatly exaggerated in the drawing FIGs.

For expository purposes, the term "horizontal" as used herein is defined as a plane parallel to the Earths horizon and perpendicular to Earths gravitational pull. The term "vertical" refers to a direction perpendicular to the horizontal as just defined. Terms, such as "above", "below", "bottom", "top", "side", "higher", "lower", "upper", "over", and "under", are defined with respect to the horizontal plane.

For the purposes of this application, substantially similar, or substantial similarity should be evaluated based on a totality of the circumstances and should be found where any difference produces no material effect.

For the purposes herein, imaging parameters includes all conditions within the environment or within the image-capturing device during capture. This can include lighting levels, lighting hues, camera orientation, camera distance, camera movement, camera settings, and background clutter.

Referring now to FIG. 1, therein is shown a block diagram of the image system 100. The image system 100 can include elements of a distributed computing system 102 including servers 104, routers 106, and other telecommunications infrastructure.

The distributed computing system 102 can include the Internet, a wide area network (WAN), a metropolitan area network (MAN), a local area network (LAN), a telephone network, cellular data network (e.g., 3G, 4G) and/or a combination of these and other networks (wired, wireless, public, private or otherwise).

The servers 104 can function both to process and store data for use on user devices 108 including laptops, cellular phones, tablet computers, and cameras, for example. It is contemplated that the servers 104 and the user devices 108 can individually comprise a central processing unit, memory, storage and input/output units and other constituent components configured to execute applications including software suitable for displaying user interfaces, the interfaces optionally being generated by a remote server, interfacing with the cloud network, and managing or performing capture, transmission, storage, analysis, display, or other processing of data and or images.

The servers 104 and the user devices 108 of the image system 100 can further include a web browser operative for, by way of example, retrieving web pages or other markup language streams, presenting those pages or streams, executing scripts, controls and other code on those pages or streams, accepting user input with respect to those pages or streams, and issuing HTTP requests with respect to those pages or streams. The web pages or other markup language can be in HAML, CSS, HTML, Ruby on Rails or other conventional forms, including embedded XML, scripts, controls, and so forth as adapted in accord with the teachings hereof. The user devices 108 and the servers 104 can be used individually or in combination to store and process information from the image system 100 in the form of operation method steps such as detecting steps, calculating steps, and displaying steps.

The user devices 108 can also be image-capturing devices 110, such as the cellular phone, a camera, a laptop, or a tablet computer. It is contemplated that the image-capturing device 110 can be any device suitable for acquiring images and communicating the images to the distributed computing system 102 and is generally depicted herein, for ease of description, as a cellular phone.

The image-capturing device 110 can be oriented toward an object with an angular position including a tilt 112, a pan 114, and a yaw 116. The tilt 112 can be the angular position of the image-capturing device 110 within a vertical plane.

The pan 114 can be the angular position of the image-capturing device 110 within a horizontal plane. The yaw 116 can be the angular position of the image-capturing device 110 rotationally about an axis extending between the image-capturing device 110 and an object being photographed.

The image-capturing device 110 can further be oriented toward an object with a distance 118 between the object and the image-capturing device 110. The distance 118, can for example, be detected as a focal distance.

The image-capturing devices 110 can be used to capture and display original images 120 of a subject 122. It is contemplated that the subject 122 can be people, objects, pictorial representations such as photographs or drawings, and models. For descriptive clarity, as used herein, the subject 122 refers to a hand, a foot, or a leg but is not limited thereto.

In addition to the original image 120, which will be discussed below with respect to FIG. 2, a skin isolated image 124 is depicted and is discussed below with regard to FIG. 3, a background 126 is depicted and is discussed below with regard to FIG. 7, a subsequent image 128 is depicted and is discussed below with regard to FIG. 8, and a problematic image 130 is depicted and is discussed below with regard to FIGS. 17-21.

It is contemplated that the original image 120 and the subsequent images 128 of the subject 122 can be included into an image history 132. The image histories 132 can be uniquely generated for an individual body part 134 of the subject 122. The body part 134 can be contained within an image frame 136.

The image frame 136 can include the body part 134 of the subject 122 entirely within the image frame 136. A region-of-interest 138 can be defined on the body part 134 of the subject 122 within the image frame 136.

Figure 2:
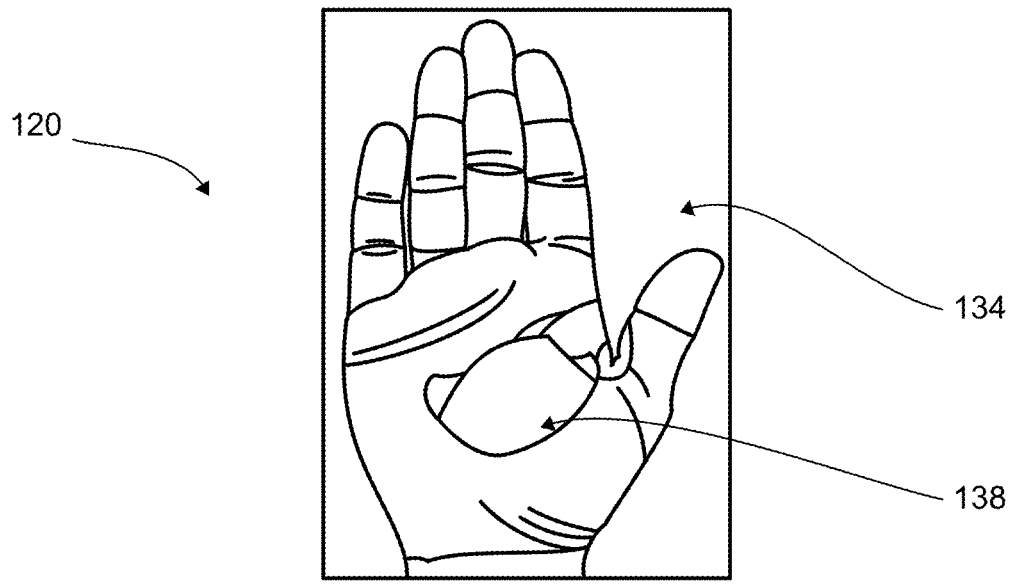
FIG. 2 is the original image of FIG. 1.

Referring now to FIG. 2, therein is shown the original image 120 of FIG. 1. The original image 120 can be the first image in a series. For example, the series could be the image history 132 of FIG. 1.

The original image 120 can include the region-of-interest 138 for the body part 134 of the subject 122 of FIG. 1. During the capture of the original image 120, the image system 100 can track several imaging parameters for the original image 120. The imaging parameters of the original image 120 can include exposure time, focus distance, ISO speed, camera position, camera movement, and focus, among other parameters. These are discussed in greater detail below with regard to FIG. 23.

Figure 23:
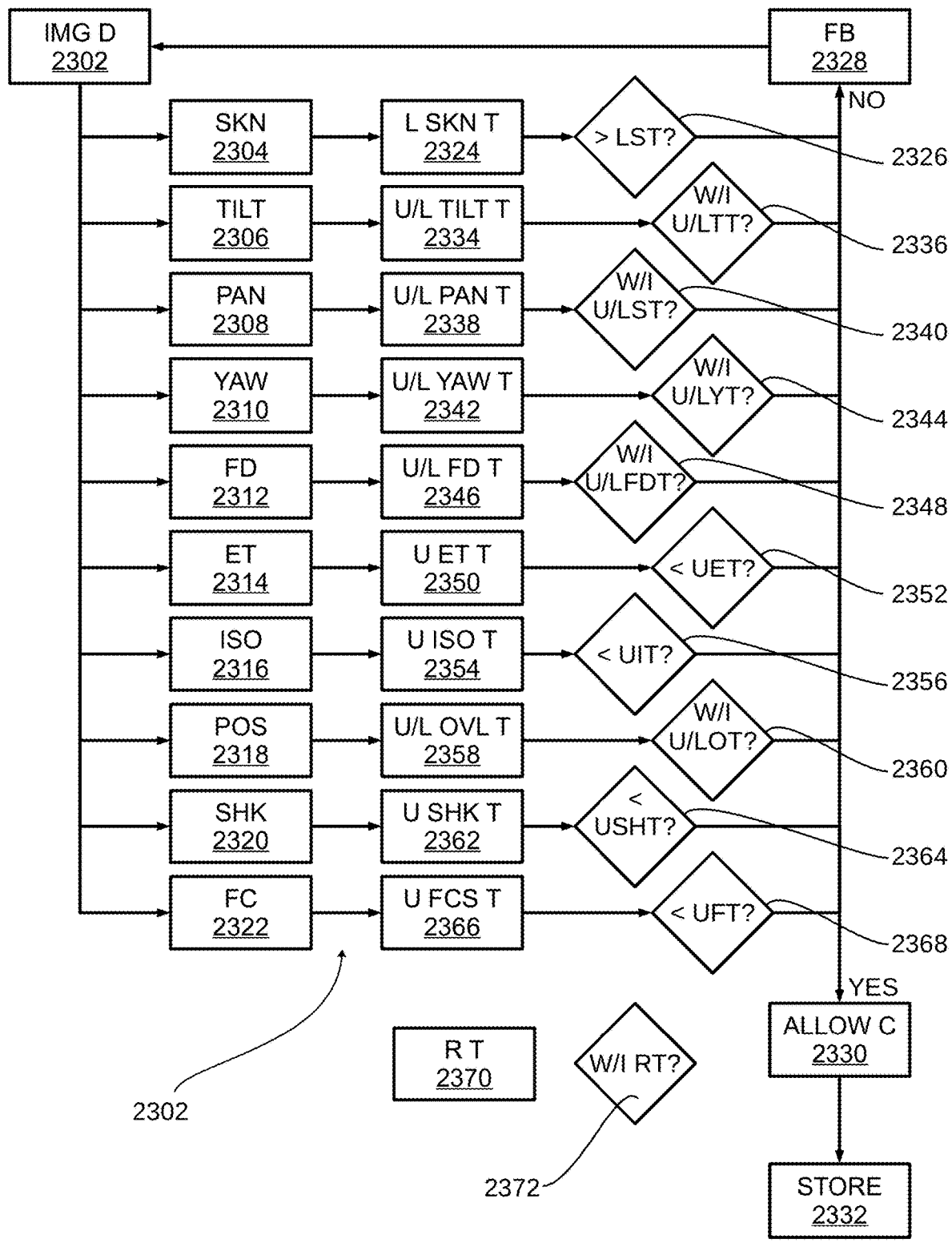
FIG. 23 is a control flow for the image system.

If the imaging parameter of the original image 120 fall outside of the thresholds of FIG. 23 governing the imaging parameters, the original image 120 will not be captured until the imaging parameters of the original image 120 are within the image thresholds.

Further, the imaging parameters of the original image 120 are compared to the same imaging parameters of the subsequent images 128 of FIG. 1 or the imaging parameters can be compared even between different subsequent images 128. If the subsequent images 128 have imaging parameters that fall outside thresholds, the subsequent image 128 will not be captured until the thresholds are met.

Further, the subsequent images 128 can be required to comply with relational thresholds. The relational thresholds govern the difference between the imaging parameters of the original image 120 or a different subsequent image 128 and the subsequent image 128 currently being captured by the image-capturing device 110 of FIG. 1.

For instance, if the distance between the body part 134 and the image-capturing device 110 is two meters for the original image 120, the overall image threshold may be from half of a meter to three meters. Subsequent images 128 must meet this overall image threshold for distance but must also meet relational thresholds relative to another image.

Continuing with the example above, if the body part 134 is two meters away from the image-capturing device 110 in the original image 120, then the body part 134 should be two meters plus or minus the relational threshold; which can for example, be half a meter. That said, in this example, the body part 134 must be two meters plus or minus half a meter from the image-capturing device 110 in order to comply with both the overall image threshold and the relational threshold.

Feedback provided to the subject 122 by the image system 100 can include arrows signaling the user to move the image-capturing device 110 closer to the body part 134 or farther from the body part 134. The feedback can further include phrases including "move closer" or "move farther away".

The feedback can provide instructions using visual, audio, or haptic feedback. For example, text can be displayed, color shading can be overlaid, directional arrows can be displayed, symbols can be animated, auditory instructions spoken, or haptic movements and signals output.

When capturing the original image 120 or any of the subsequent images 128, it is contemplated that the image thresholds and the relational thresholds can be used to generate the feedback for the user. For example, if the scene is too dark and fails to comply with either the overall image threshold or the relational threshold for lighting, the image system 100 can provide the instruction: "Use brighter lighting" either by text, displaying symbols, or by auditory signal.

As a further example, if the scene includes harsh shadows, the image system 100 can provide the instruction: "Use more diffuse lighting". It is contemplated that harsh shadows or other background artifacts can be identified by utilizing light markers and dark markers or by implementing a histogram algorithm.

As yet a further example, if the image-capturing device 110 is not level with regard to the overall image threshold or is rotated greater than the relational threshold with regard to a previously taken image, such as the original image 120 or another subsequent image 128, the image system 100 can provide rotational instructions using arrows showing the direction of rotation required to comply with both thresholds.

Figure 3:
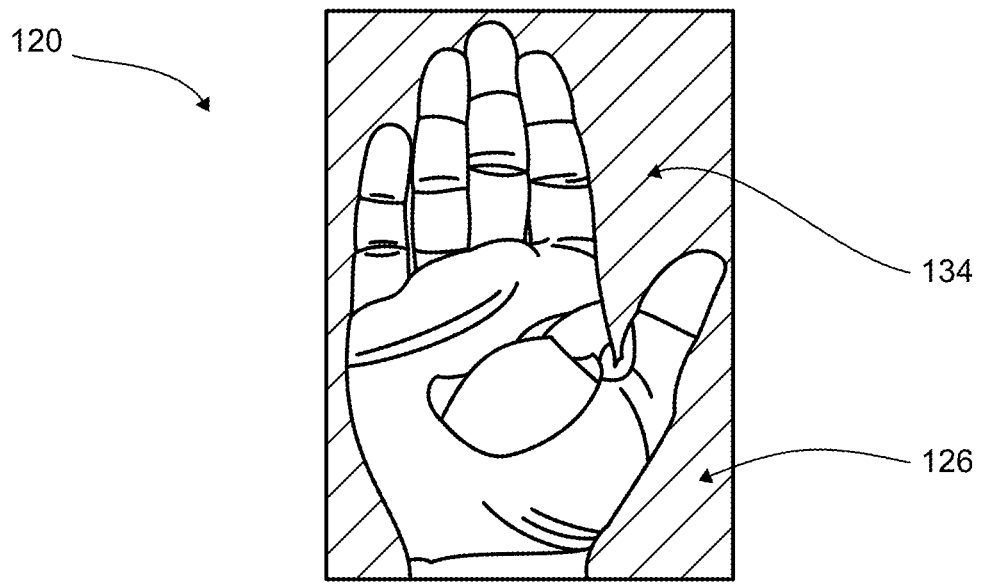
FIG. 3 is the original image of FIG. 1 in a skin isolation step.

Referring now to FIG. 3, therein is shown the original image 120 of FIG. 1 in a skin isolation step. The original image 120 of FIG. 1 can be used to define an overlay to be used on the subsequent images 128 of FIG. 1 within the image history 132 of FIG. 1.

Illustratively, for example, the background 126 can be isolated from the skin of the body part 134 of the subject 122 of FIG. 1. The background 126 can be used as the overlay for subsequent image captures.

Figure 4:
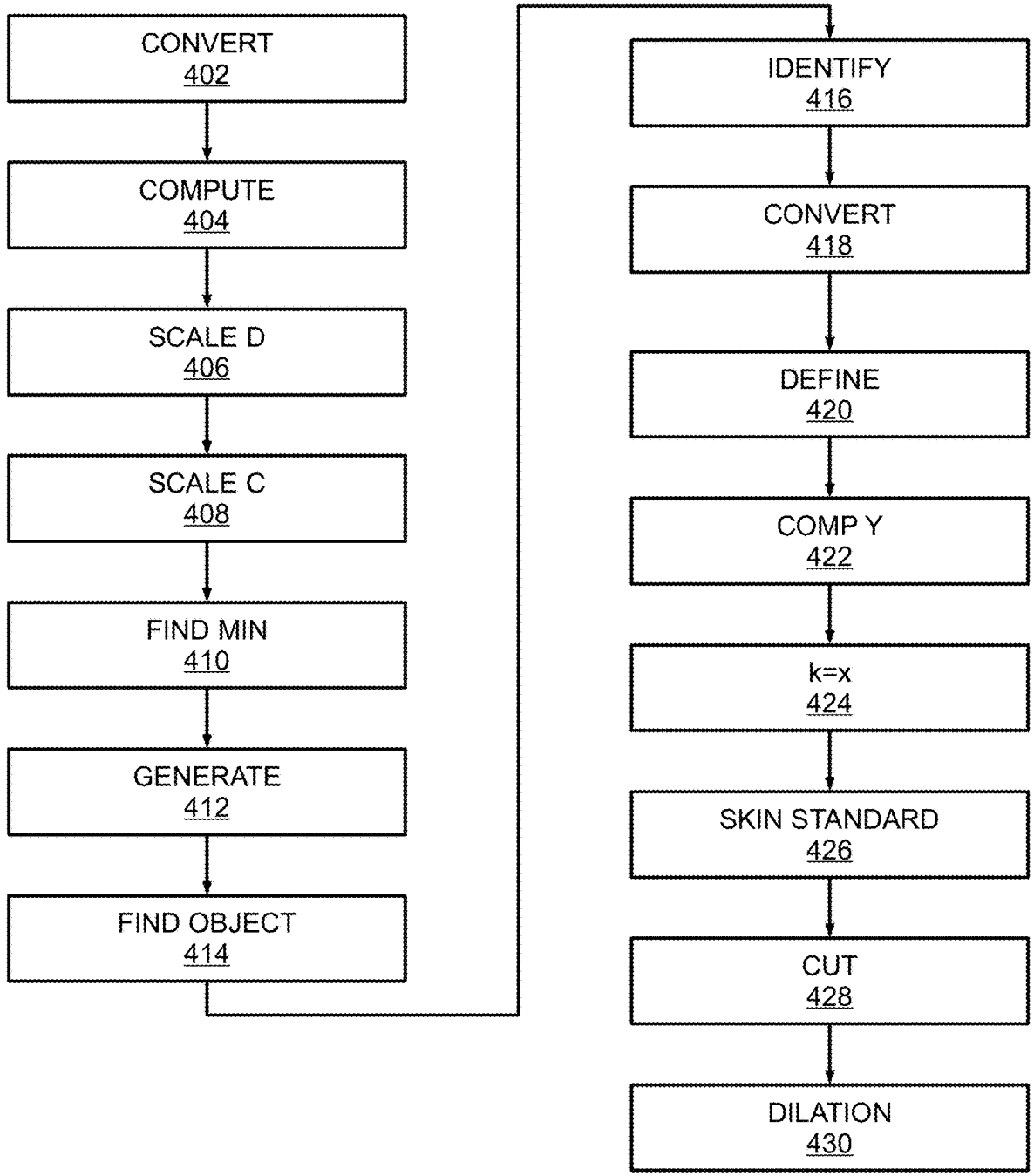
FIG. 4 is a control flow for YCrCb skin selection.

Referring now to FIG. 4, therein is shown a control flow for YCrCb skin selection. It is contemplated that the control flow can be implemented as a series of process steps.

The process steps may be instructions stored on a non-transitory computer-readable medium, that when executed by a processor, perform the process steps. Those of ordinary skill in the art will recognize that the steps can be performed in any order —except where order is required by the context or elements of an individual step—steps may be broken into multiple smaller steps or contained into fewer larger steps without deviating from the skin color system as disclosed herein.

For this YCrCb skin selection control flow, the input parameters are: skin standard {CrSS, CbSS}; cut off adjustment (6), which can typically be 0.02; and a dilation kernel for thickening an outline kern. For clarity of description, the term "kern" is used herein as a parameter that defines the size of the dilation kernel; for mathematical neatness it probably should be $k_D$ (a single character k for Dilation). The kernel is a $k_D$ by $k_D$ matrix of 1 and zeros. For implementation the variable "kern" is convenient.

The YCrCb control flow can include a convert step 402. The convert step 402 can convert an image to YCrCb color space. This can include the original image 120 of FIG. 1 or the subsequent image 128 of FIG. 1.

The YCrCb control flow can further include a compute step 404. The compute step can be executed to compute skin-color distance from standard skin. The compute step 404 can be accomplished by computing $D_S^2=(Cr-CrSS)2+(Cb-CbSS)2$; where Cr and Cb are the image components in YCrCb, and CrSS and CbSS are single values for "standard skin".

The YCrCb control flow can further include a scale D step 406. The scale D step 406 can scale $D_S^2$ in the range 0 to $1-D_S^2$.

The YCrCb control flow can further include a scale C step 408. The scale C step 408 can scale Cr in the range 0 to 1-Cr.

The YCrCb control flow can further include a find min step 410. The find min step 410 can find the minimum cut off k in Cr that satisfies minimum $D_S$ as will be described with regard to define step 420, compute Y step 422, and k=x step 424.

The YCrCb control flow can further include a generate step 412. The generate step 412 can generate a binary image I where Cr<k=0.

The YCrCb control flow can further include a find object step 414. The find object step 414 can find distinct objects OJ within I. I can be the original image 120. Distinct objects OJ in a binary image can be groups of non-zero pixels that are adjacent to each other, that is the non-zero pixels touch by edge or corner. To be distinct the distinct object OJ has no border connections with other objects. These can be computed, for example, by Connected Components Algorithm in openCV cv2.connectedComponents.

The YCrCb control flow can further include an identify step 416. The identify step 416 can identify the largest object OS as skin. The YCrCb control flow can further include a convert step 418. The convert step 418 can convert OS to a mask or an outline, such as the background 126 of FIG. 1.

The YCrCb control flow can further include multiple steps for finding the minimum cut off k in Cr that satisfies minimum $D_S^2$, as for example is included in the find min step 410. These steps can include a define step 420, a compute Y step 422, and a k=x step 424.

The define step 420 can define a broader skin range for Cr 0.35 to 0.75⇒x for skin it is 0.50 to 0.68. The full range of Cr is 0 to 1. While the broader skin range is described for Cr as 0.35 to 0.75, it will be understood by those of ordinary skill in the art that the skin rage for Cr can be narrower or wider.

The compute Y step 422 can compute a Y value for each of the x values defined in the define step 420. Y is defined as: $Y(x) = mean(D_S^2 \text{ for } Cr<x)/mean(D_S^2)$ The k=x step 424 can compute where k=x where Y(x) is a minimum (6). 6 can be a small adjustable parameter.

Figure 5:
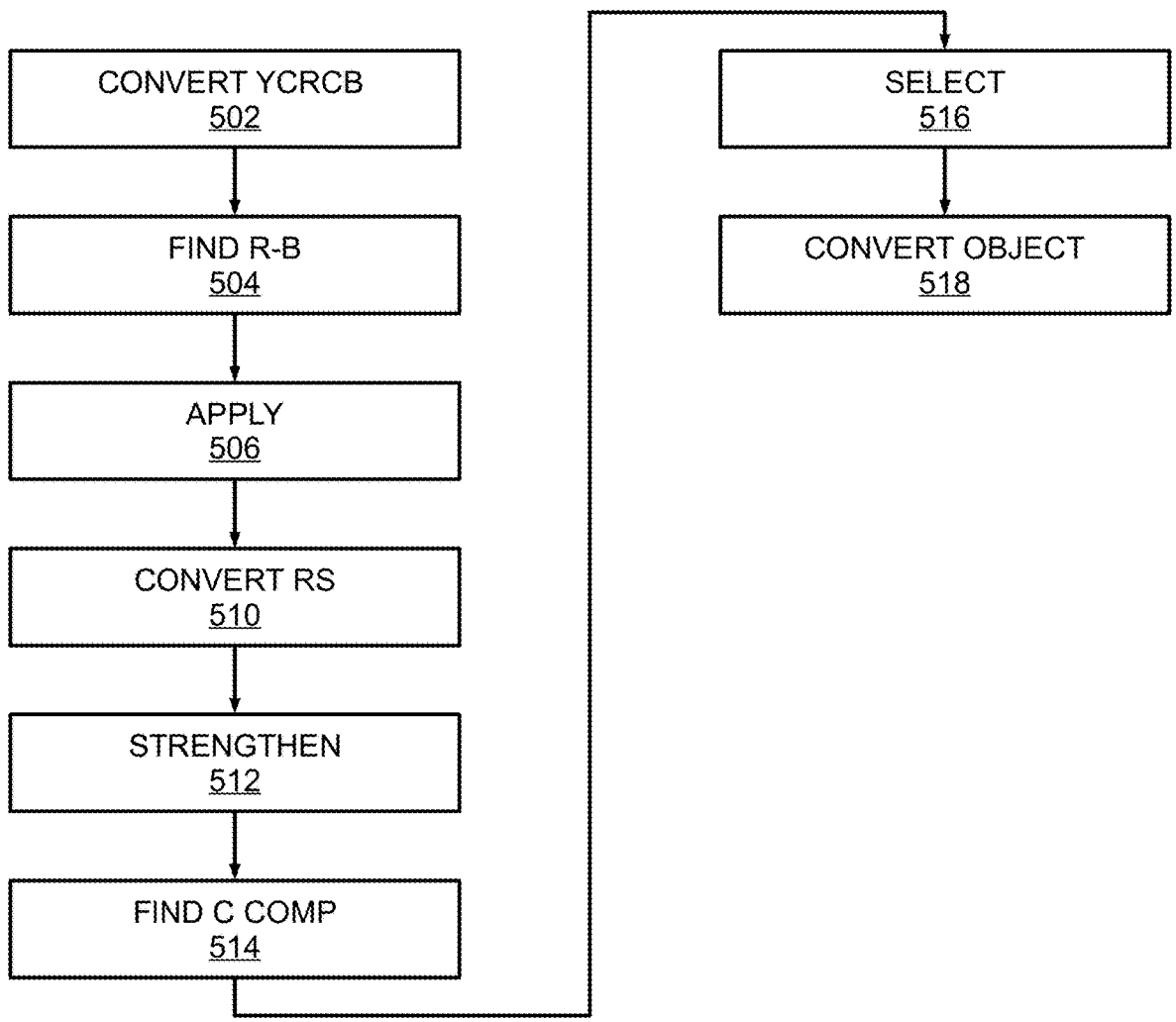
FIG. 5 is a control flow for RGB skin selection.

Referring now to FIG. 5, therein is shown a control flow for RGB skin selection. It is contemplated that the control flow can be implemented as a series of process steps.

The process steps may be instructions stored on a non-transitory computer-readable medium, that when executed by a processor, perform the process steps. Those of ordinary skill in the art will recognize that the steps can be performed in any order —except where order is required by the context or elements of an individual step—steps may be broken into multiple smaller steps or contained into fewer larger steps without deviating from the skin color system as disclosed herein.

For this RGB skin selection control flow, a bilateral filter can be implemented, the input parameters can include: d, the Diameter of each pixel neighborhood that is used during filtering; sigmaColor, a filter sigma in the color space; and sigmaSpace, a filter sigma in the coordinate space.

Edge detection can also be included in the RGB skin selection control flow, the input parameters can include: kg, which can be the kernel size Gaussian blur for Sobel filter; ks, which can be the size of the extended Sobel kernel, it must be 1, 3, 5, or 7, with 5 currently understood as best; and scut. Scut can be "k" in the convert Rs step 510 discussed below. The Sobel filter can be a Sobel-Feldman operator or Sobel filter, which can be used in image processing and computer vision, particularly within edge detection algorithms where it creates an image emphasizing edges.

Morphological operations can also be included in the RGB skin selection control flow, the input parameters can include: Kern, which can be a kernel for dilate and open operations; N1, which can be the number of erode operations, six is typical; and N2, which can be the number of open operations, ten is typical. Kern set to 5 has been discovered to be an optimal setting.

The RGB control flow can include a convert YCRCB step 502. The convert YCRCB step 502 can convert image to YCrCb and find the skin distance $D_S^2$ as described above with regard to the YCrCb selector of FIG. 4.

The RGB control flow can include a find R-B step 504. The find R-B step 504 can find R-B, can sharpen with a bilateral filter, and can scale 0 to 1 range⇒R. The RGB (red green blue) color space can be either defined as an integer with each of the three channels ranging from 0 to 255 or a floating number in the range of 0.0 to 1.0—which is what can be used during the find R-B step 504 to find R-B. R-B can be the subtraction of the Blue channel from the Red. The range for this can be negative one to positive one. A bilateral filter, for example in openCV, can be implemented to filter for sharpening edges with some smoothing by avoiding a sharpening on noise.

The RGB control flow can include a combine step 506. The apply step 506 can apply Sobel X and Y filters separately (use Gaussian pre-blur). The absolutes of the Sobel filters ⇒ $R_S$.

The RGB control flow can include a convert $R_S$ step 510. The convert $R_S$ step 510 can convert $R_S$ to binary I ($R_S$>k) =0. k is a cutoff typically 0.25.

The RGB control flow can include a strengthen step 512. The strengthen step 512 can strengthen the binary I with morphological operations erode and open.

The RGB control flow can include a find c comp step 514. The find c comp step 514 can find connected components in I i.e. distinct objects OJ.

The RGB control flow can include a select step 516. The select step 516 can select an object sorted by size and minimum skin distance DS2.

It has been discovered that minimum skin distance can be used here since at times the background could be the largest object and not skin. The object can be ⇒ OS. This is not a problem with the YCrCb control flow of FIG. 4 since skin distance is used at the beginning of the control flow.

The RGB control flow can include a convert object step 518. The convert object step 518 can convert OS to a mask or an outline such as the background 126 of FIG. 1.

The YCrCb skin selection of FIG. 4, the RGB skin selection of FIG. 5 are therefore directed to an improvement in computer-related technology. The control flow process steps of FIGS. 4 and 5 allow the distributed computing system 102 of FIG. 1 to produce accurate and realistic skin detection and selection with digital images that previously could only be produced by humans. Thus, the steps of FIGS. 4 and 5 are specific steps that accomplish the result of color selection in a digital image that realizes an important improvement in computer imaging functionality.

Figure 6:
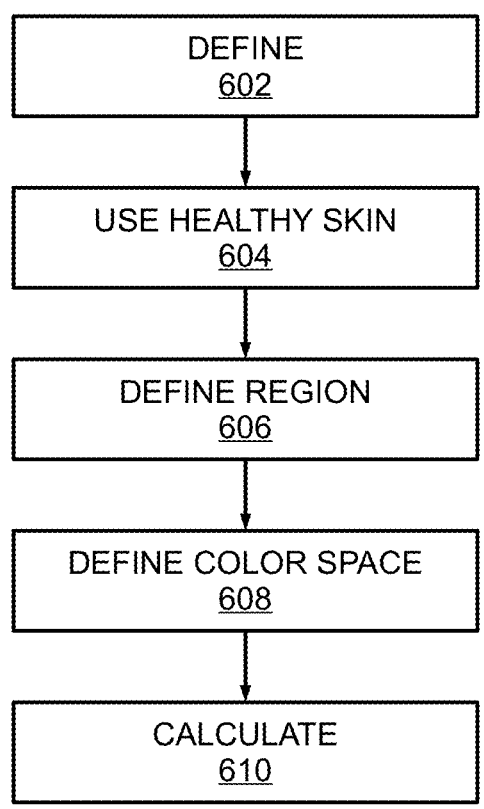
FIG. 6 is a control flow for color correction.

Referring now to FIG. 6, therein is shown a control flow for color correction. It is contemplated that the control flow can be implemented as a series of process steps.

The process steps may be instructions stored on a non-transitory computer-readable medium, that when executed by a processor, perform the process steps. Those of ordinary skill in the art will recognize that the steps can be performed in any order —except where order is required by the context or elements of an individual step—steps may be broken into multiple smaller steps or contained into fewer larger steps without deviating from the skin color system as disclosed herein.

The color correction control flow can include a define step 602. The define step 602 can define a standard. The standard can either be a set of "numbers" or a section of a reference image. "Numbers" can be generated if the standard is part of an image.

The color correction control flow can further include a use healthy skin step 604. The use healthy skin step 604 can use healthy skin, not the wound or healing skin when color correcting for skin.

Healthy skin can be determined by the system. Illustratively, for example in a typical YCbCr color space chart, healthy skin is the skin that most closely resembles the standard skin in the Cr and Cb channels.

It is contemplated that thresholds and statistical deviations can be used to determine the relatedness of healthy skin to the Cr and Cb channels. For example, any skin that lies inside the range of Cr, Cb can be identified as normal or healthy skin.

In the case of an image with a wound and healthy skin, the Cr, Cb distribution will have two distinct region or zones that can be distinguished with thresholds or unsupervised machine learning methods such as clustering. The color correction control flow can further include a define region step 606.

The define region step 606 can define a region of the image to be corrected. The region should be representative of the skin or object in need of correction. The region should not be the background. The color correction control flow can further include a define color space step 608. The define color space step 608 can define color space and channels.

It is contemplated that a color space conversion may be used during the define color space step 608. In some cases, further computation on channels may be needed. The channels can be a grey scale image of each of the RGB colors. In different color spaces other channels may be defined. The color correction control flow can further include a calculate step 610. The calculate step 610 can compute mean and standard deviation per channel.

The calculation can include: let $C_i$ be a color channel prior to correction, let $C_j$ be a color channel after to correction, let $C_R$ be a color channel of the reference image. A set of numbers for correction can be $\{mean(C_i), std(C_i)\}$ i=1, 2, 3; and $\{mean(C_R), std(C_R)\}$ R=1, 2, 3. The correction formula can be one of the two forms: the first being $C_j=[C_i-mean(C_i)]*[std(C_R)/std(C_i)]+mean(C_R)$; and the second being $C_j=C_i-mean(C_i)+mean(C_R)$.

It is contemplated that for the {R-B, R-G} correction the channels $C_i$ are {V, R-B, R-G}, where V=R+G+B. The correction formula can be the same as previous ones but can be expanded to one of three forms: the first being $C_j=(mean(V_R)/mean(V_j)*([C_i-mean(C_i)]*[std(C_R)/std(C_i)]+mean(C_R))$; the second being $C_j=[C_i-mean(C_i)]*[std(C_R)/std(C_i)]+mean(C_R)$; and the third being $C_j=C_i-mean(C_i)+mean(C_R)$. $V_j=(mean(V_R)/mean(V_j)*V_i$; OR $V_j=V_i$.

The correction formula for the red channel can be $R_{CORR}=(C_{j=R-B}+C_{j=R-G}+V_H)/3$. The correction formula for the blue channel can be $B_{CORR}=R_{CORR}\ C_{j=R-B}$. The correction formula for the green channel can be $G_{CORR}=R_{CORR}-C_{j=R-G}$.

The color correction of FIG. 6 is therefore directed to an improvement in computer-related technology. The control flow process steps of FIG. 6 allow the distributed computing system 102 to produce accurate and realistic color correction in digital images that previously could only be produced by humans, with a process not known to be used by humans.

Thus, the steps of FIG. 6 are specific steps that accomplish the result of color correction in a digital image that realizes an important improvement in computer imaging functionality.

It has been discovered that the steps of FIGS. 4-6 can improve computer related technologies in other ways as well. This can include the reduction in computational overhead in the form of memory requirements, processing requirements, and data transmission requirements stemming from the effective use of color corrected images with identified skin and not requiring large quantities of less effective images without skin identification and color correction.

Figure 7:
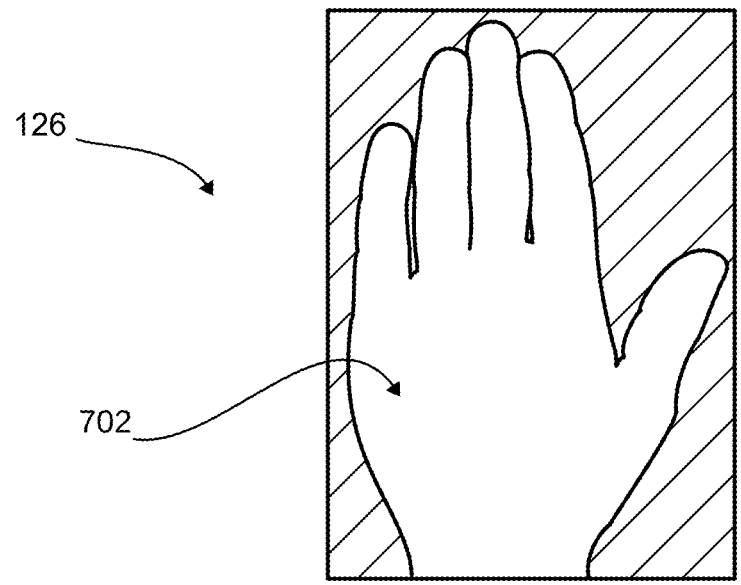
FIG. 7 is the background of the original image of FIG. 1.

Referring now to FIG. 7, therein is shown the background 126 of the original image 120 of FIG. 1. The background 126 can be used as an overlay and, for example, can be overlaid on the image-capturing device 110 of FIG. 1 during subsequent image capture as, for example, is described with regard to FIGS. 9, 10, and 11.

The background 126 can be anything that is not skin and lies near the edges of the original image 120. It has been found that there are few effective ways to determine extraneous objects in the image other than skin identification.

The skin amount detected can be compared with the skin amount detected within previous images such as the original image 120 or previously taken subsequent images 128 of FIG. 1. Image capture can be rejected if too much skin is detected. Increasing skin area within a series of images can be a red flag.

Three things can happen in skin identification: 1) only the body part will be identified as skin so that extraneous objects will automatically fail into the background; 2) an object in the background will fulfill the skin match test, but it will be rejected on size with the assumption that the largest separable object is the body part of interest (separable means that a distinct boundary is found between the object of interest and the extra object); or 3) an object in the background will fulfill the skin match test and is too close to the object of interest such that the two objects will be considered as one. If the objects are not separable, an error would result.

Figure 8:
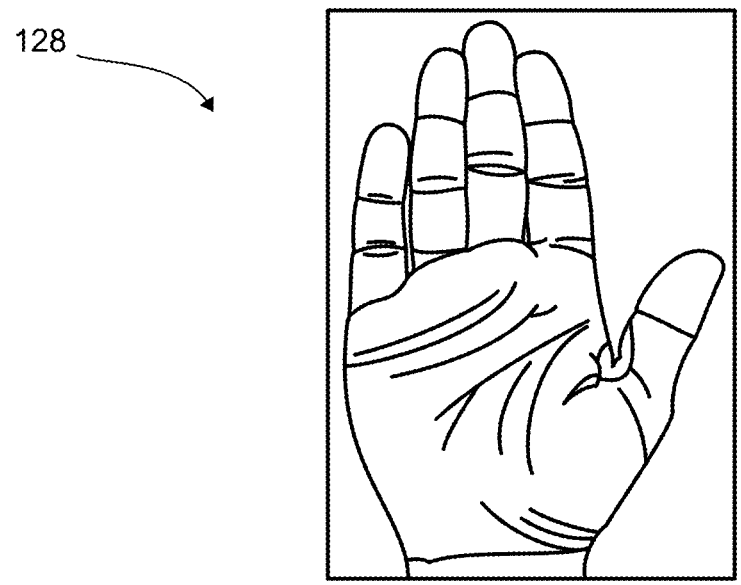
FIG. 8 is the subsequent image of FIG. 1.
Figure 9:
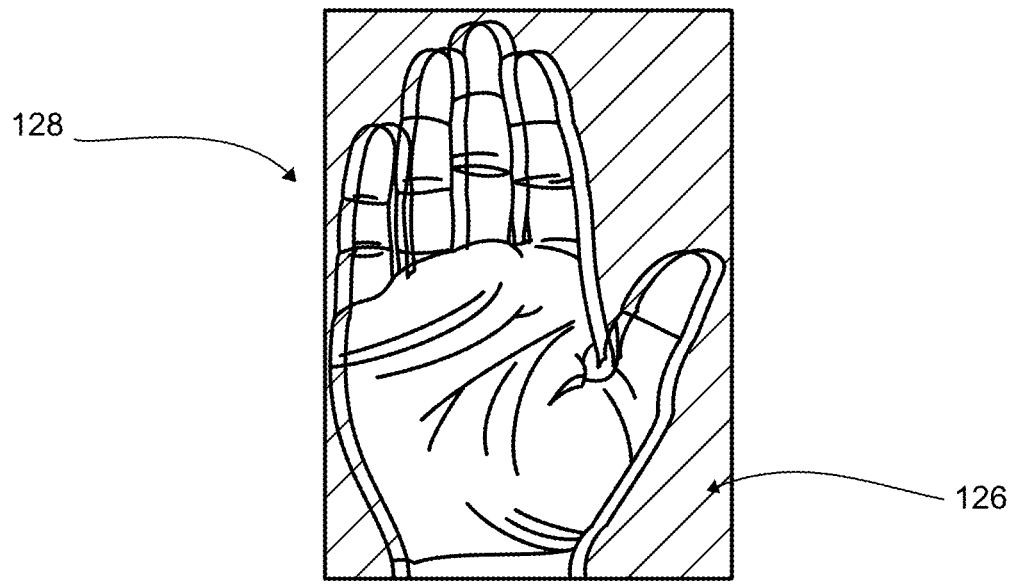
FIG. 9 is the subsequent image of FIG. 8 in a first alignment step.
Figure 10:
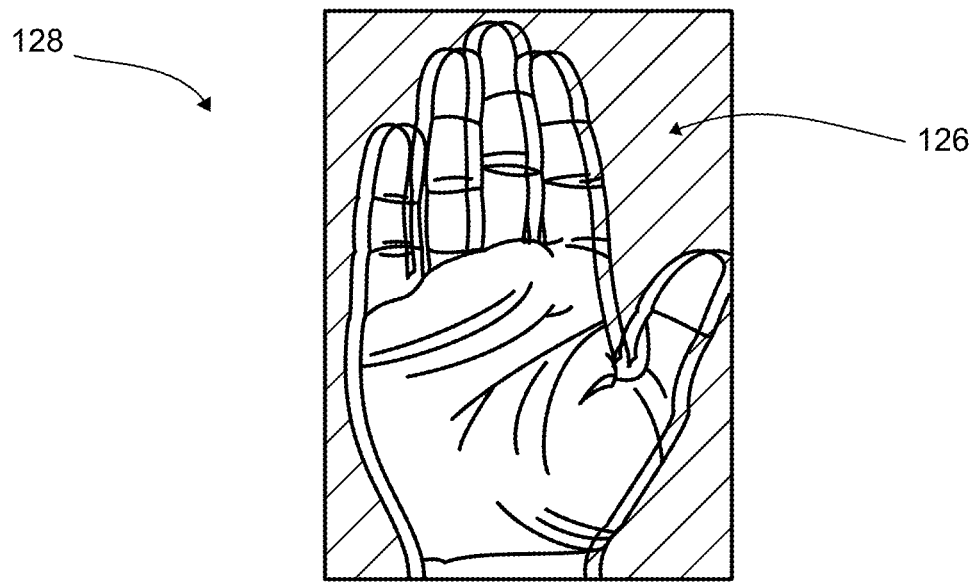
FIG. 10 is the subsequent image of FIG. 8 in a second alignment step.

Illustratively, the overlays on the subsequent images 128 of FIGS. 9 and 10 are not properly aligned. It is contemplated that the exposure integrity program will prevent the user device 108 from capturing the subsequent image 128 while the misalignment is detected. Rather, the operator of the user device 108 will be instructed to move so as to match the background with the subsequent image 128 as is shown in FIG. 8, for example.

Only once a match has occurred will the exposure integrity program allow the capture of the subsequent image 128. However, in some circumstances, when automated image correction is able to compensate for poor imaging parameters, as described in FIG. 5 for example, image capture will be allowed and the image later corrected.

Referring now to FIG. 8, therein is shown the subsequent image 128 of FIG. 1. The subsequent image 128 can illustratively depict the body part 134 of FIG. 1 of the subject 122 of FIG. 1 later in the time chronology relative to the original image 120 of FIG. 1. The subsequent image 128 can depict the body part 134 with the region-of-interest 138 of FIG. 1 showing a healed surface.

Referring now to FIG. 9, therein is shown the subsequent image 128 of FIG. 8 in a first alignment step. When aligning the body part 134 of FIG. 1 of the subject 122 of FIG. 1, the user or the subject 122 can move the camera and hand left, right, toward the camera, away from the camera, and rotationally.

The background 126 can be overlaid over the subsequent image 128 for ensuring proper alignment of the body part 134 of the subject 122 with the position of the body part 134 in the original image 120 of FIG. 1; or in the alternative, to the position of the body part 134 within an earlier acquired subsequent image 128. As will be appreciated, the background 126 in relation to the body part 134 of FIG. 9 requires the image-capturing device 110 of FIG. 1 to be moved left and down with respect to the body part 134 or in the alternative, the body part 134 could be moved up and right by the subject 122.

It is contemplated that when the body part 134 is not in alignment with the overlaid background 126, the image system 100 can generate instructions including: "move hand right and up" or "move camera down and left".

Referring now to FIG. 10, therein is shown the subsequent image 128 of FIG. 8 in a second alignment step. When aligning the body part 134 of FIG. 1 of the subject 122 of FIG. 1, the user or the subject 122 can move the camera and hand left, right, toward the camera, away from the camera, and rotationally.

The background 126 can be overlaid over the subsequent image 128 for ensuring proper alignment of the body part 134 of the subject 122 with the position of the body part 134 in the original image 120 of FIG. 1; or in the alternative, to the position of the body part 134 within an earlier acquired subsequent image 128. As will be appreciated, the background 126 in relation to the body part 134 of FIG. 9 requires the image-capturing device 110 of FIG. 1 to be moved right and up with respect to the body part 134 or in the alternative, the body part 134 could be moved down and left by the subject 122.

It is contemplated that when the body part 134 is not in alignment with the overlaid background 126, the image system 100 can generate instructions including: "move hand right and down" or "move camera left and up".

Figure 11:
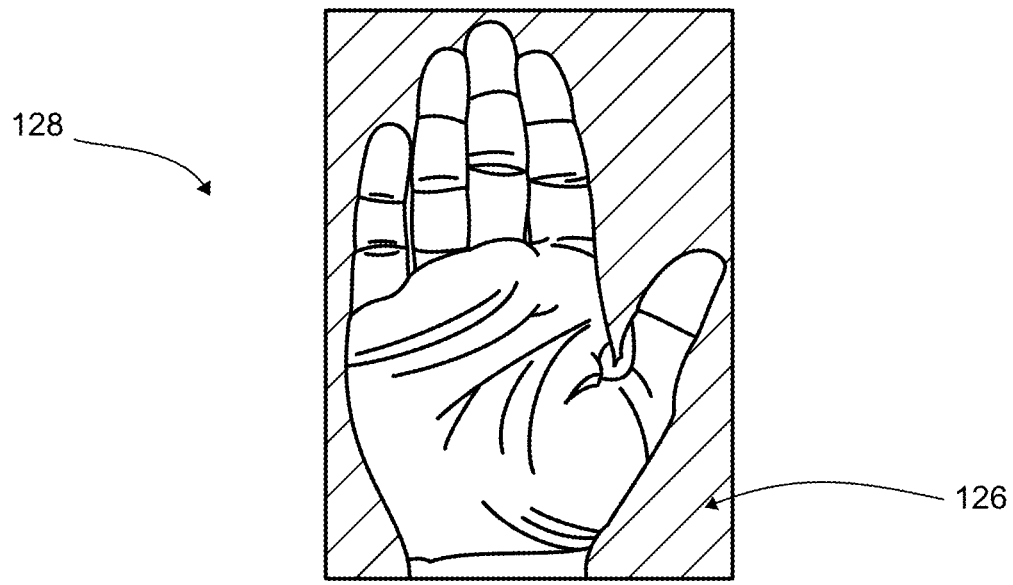
FIG. 11 is the subsequent image of FIG. 8 in a third alignment step.

Referring now to FIG. 11, therein is shown the subsequent image 128 of FIG. 8 in a third alignment step. When aligning the body part 134 of FIG. 1 of the subject 122 of FIG. 1, the user or the subject 122 can move the camera and hand left, right, toward the camera, away from the camera, and rotationally.

The background 126 can be overlaid over the subsequent image 128 for ensuring proper alignment of the body part 134 of the subject 122 with the position of the body part 134 in the original image 120 of FIG. 1; or in the alternative, to the position of the body part 134 within an earlier acquired subsequent image 128. As will be appreciated, the background 126 in relation to the body part 134 of FIG. 12 can be considered in alignment requiring no further adjustment of the image-capturing device 110 or the body part 134.

Figure 12:
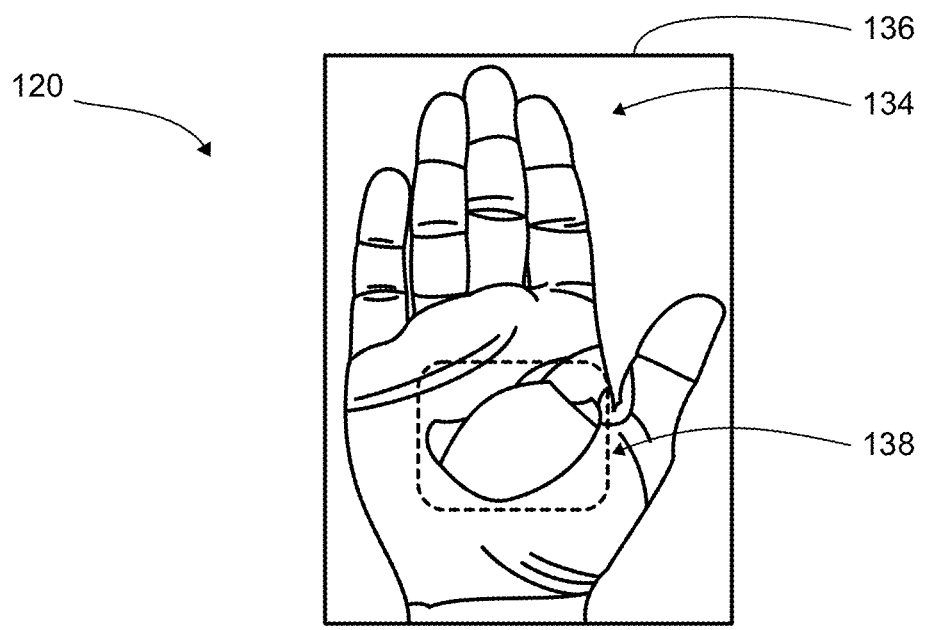
FIG. 12 is the original image of FIG. 1 with the region-of-interest defined.

Referring now to FIG. 12, therein is shown the original image 120 of FIG. 1 with the region-of-interest 138 defined. As will be appreciated, the body part 134 of the subject 122 of FIG. 1 is shown being well framed, or well positioned within the image frame 136.

Proper framing within the image frame 136 includes properly including all of the edges of the body part 134 to be photographed within the image frame 136. Further, the original image 120 is shown having a well-defined context, that is only the body part 134 to be photographed is contained within the image frame 136 other than a plain, clean, high contrast background.

For example, the original image 120 of the body part 134, showing the wounded hand, can be considered well framed. Alignment of the subsequent image 128 of FIG. 1 can be achieved via active overlay of the background 126 onto the image-capturing device 110 of FIG. 1. would not be possible as there are no "anchor" points.

It is contemplated that the original image 120 shown can be improved by increasing the distance between the left side and top side of the image frame 136 and the body part 134. This extra space would ensure that the middle finger of the body part 134 and the left side of the body part 134 are fully contained within the image frame 136 and not cut off.

Anchor points can be identified by the outlines of the fingers or fingertips. These points of high contrast can be used to align the image-capturing device 110 to the subject 122 in order to ensure the region-of-interest 138 is visible and the body part 134 aligned within the background 126.

Turning to the present example, the region-of-interest 138 can be the wound on the body part 134 of the subject 122. If the region-of-interest 138 is all that is displayed, that is a magnified region-of-interest 138, then there may be confusion as to what is exactly shown, thus providing the context of the region-of-interest 138 as a part of the body part 134 is highly beneficial to the diagnosis, analysis, and tracking of surface artifacts.

The original image 120 is depicted having the region-of-interest 138 outlined within the body part 134 and overlaid onto the body part 134 within the original image 120. It is contemplated that any numerical analysis by the image system 100 can be done within the region-of-interest 138.

The portion of the body part 134 not included within the region-of-interest 138 can therefore be considered context, for the purposes of this application. The context can be useful for alignment of the body part 134 as a whole and useful for defining healthy skin.

It has been discovered that defining healthy skin can be used for color matching between photographs. The region-of-interest 138 can be specified by a prescribing physician or medical specialist and not the patient or the subject 122.

It has been discovered that the computation and numerical analysis of healthy skin and identifying healthy skin are the reason that image integrity and repeatability should be maintained. The computation and analysis may include progression of healing by monitoring color change in a wound; monitoring the size of a lesion, wound, or rash; or counting the number of blemishes like acne pimples.

Figure 13:
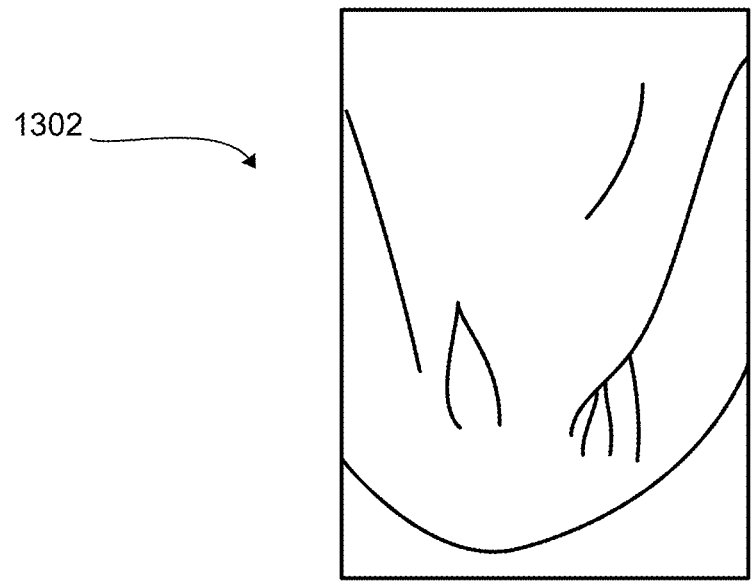
FIG. 13 is an improperly framed image.

Referring now to FIG. 13, therein is shown an improperly framed image 1302. The improperly framed image 1302 can be the region-of-interest 138 of FIG. 12 without the context of the rest of the body part 134 of FIG. 12. Specifically, the improperly framed image 1302 is too close and poorly framed resulting in undefinable content. It is contemplated that the original image 120 and the subsequent images 128 of FIG. 1 should contain the region-of-interest 138 along with the context, the context being the rest of the body part 134, useful for healthy skin detection and alignment detection.

Figure 14:
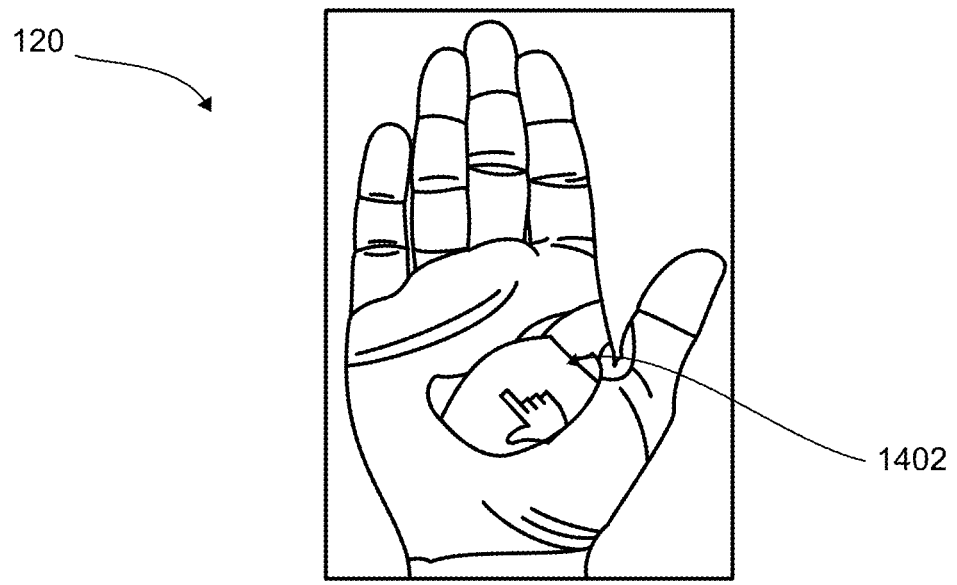
FIG. 14 is an interface for region-of-interest center point selection.

Referring now to FIG. 14, therein is shown an interface for region-of-interest center point selection. The original image 120 is shown overlaid with a selection tool 1402. The selection tool 1402 can be a pointer in the shape of a cursor, arrow, pointer, or hand. It is contemplated that a physician or medical specialist can utilize the interface and tap the original image 120 to identify the center point of the region-of-interest 138 of FIG. 1. It is contemplated that the region-of-interest center point can be selected, changed, dragged, and fixed on the user devices 108 of FIG. 1 on an interactive display screen.

Illustratively, the region-of-interest 138 can be defined by the physician, either by drawing a box or by centering the region-of-interest 138 within a preset circle or ellipse. The region-of-interest 138 definition can be a manual process conducted on the original image 120 done by the physician. The circle or ellipse can be automatic and fixed. There may be a selector circle-or-ellipse.

Figure 15:
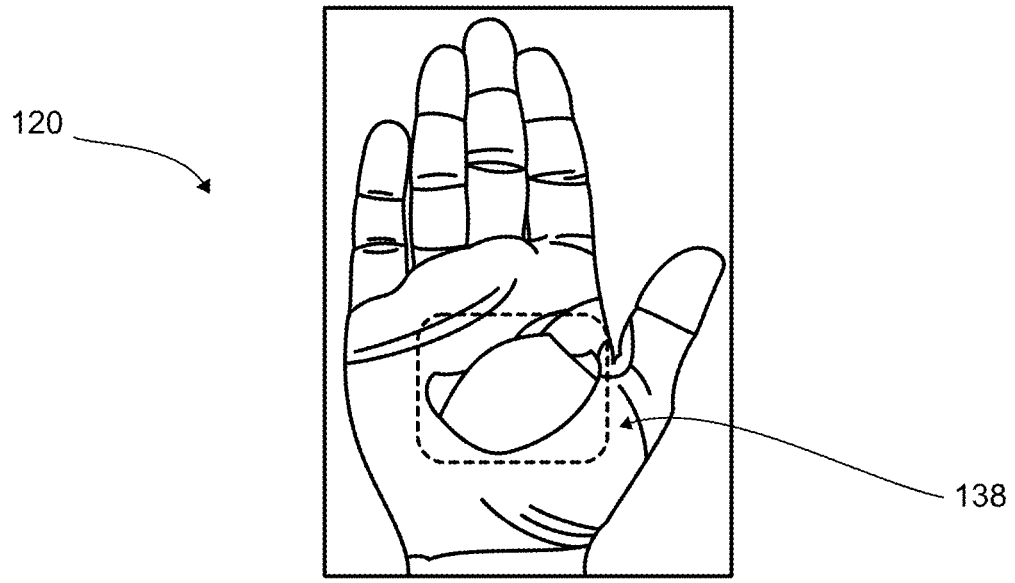
FIG. 15 is a user interface for an initial region-of-interest.

Referring now to FIG. 15, therein is shown a user interface for an initial region-of-interest. The original image 120 is depicted having the region-of-interest center point defined by the process described in FIG. 14 and having the region-of-interest 138 overlaid on the original image 120.

The region-of-interest 138 can be initially sized and shaped according to a preset template, image, or model. The region-of-interest 138 can further be created based on the size of the image frame 136 of FIG. 1 or based on the distance between the body part 134 of FIG. 1 and the image-capturing device 110 of FIG. 1.

Figure 16:
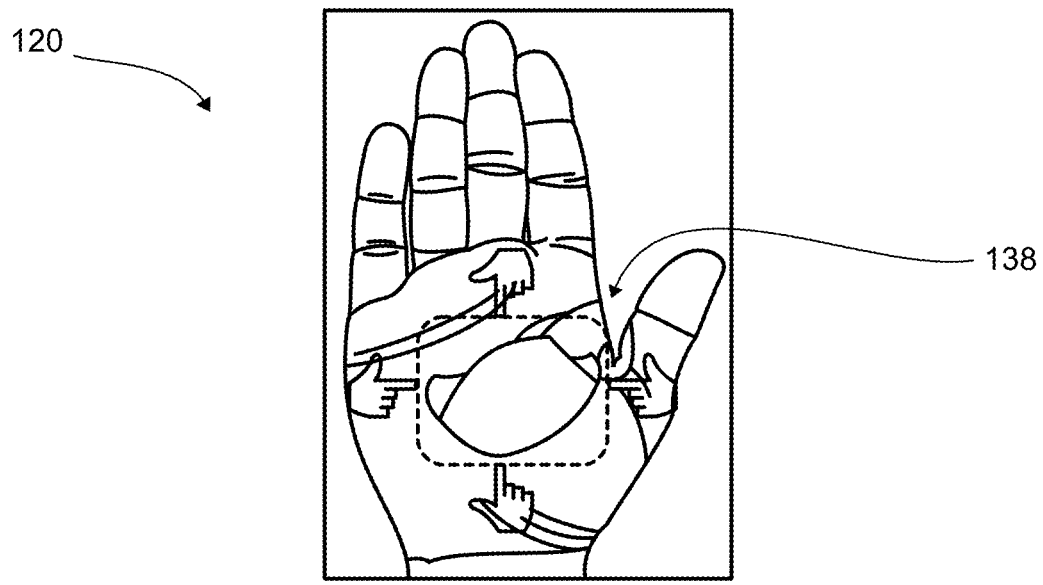
FIG. 16 is a user interface for region-of-interest adjustment.

Referring now to FIG. 16, therein is shown a user interface for region-of-interest adjustment. The region-of-interest 138 can be adjusted by dragging the edges of the region-of-interest 138 on the user device 108 of FIG. 1, which can be overlaid on the original image 120 for proper adjustment of the region-of-interest 138.

Figure 17:
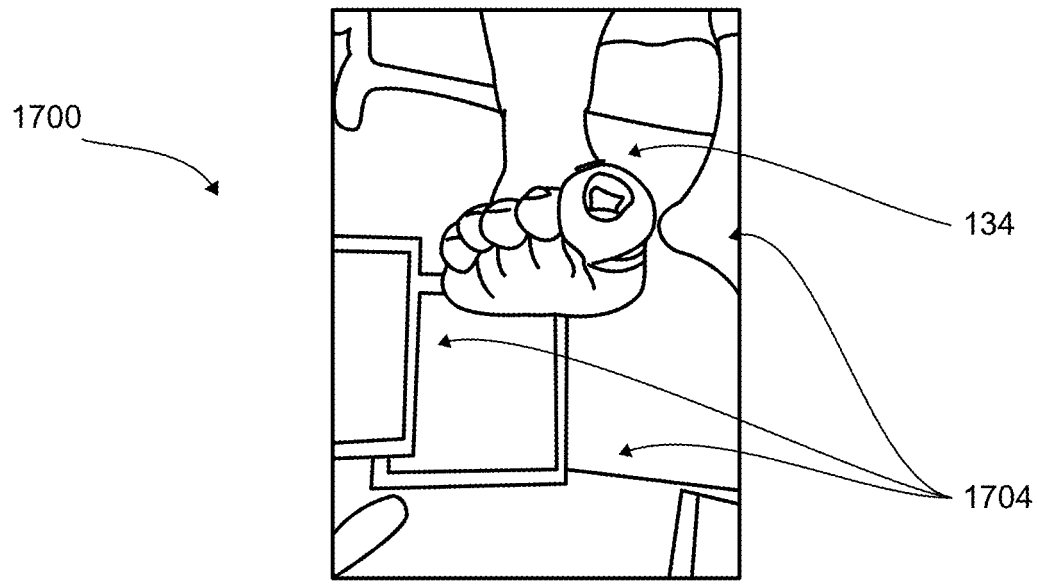
FIG. 17 is a first problematic image.

Referring now to FIG. 17, therein is shown a first problematic image 1700. The first problematic image 1700 can be understood as problematic due to background clutter 1704, and the overly close distance between the body part 134 and the image-capturing device 110 of FIG. 1. However, it must be noted that the leg line of the subject 122 of FIG. 1 is well and properly centered on the mid foot.

Figure 18:
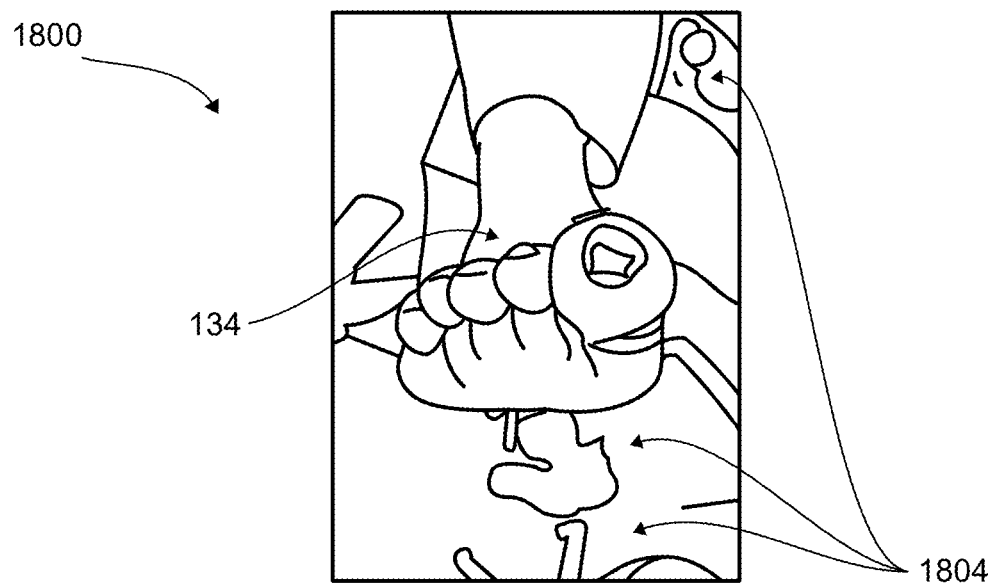
FIG. 18 is a second problematic image.

Referring now to FIG. 18, therein is shown a second problematic image 1800. The second problematic image 1800 can be understood as problematic due to background clutter 1804, and the overly close distance between the body part 134 and the image-capturing device 110 of FIG. 1. Further, the size of the body part 134, due to the body part 134 being close to the camera, is larger than the image of FIG. 17 and should be moved further from the image-capturing device 110 in order to ensure the body part 134 is a similar size to the body part 134 captured in the related images.

Figure 19:
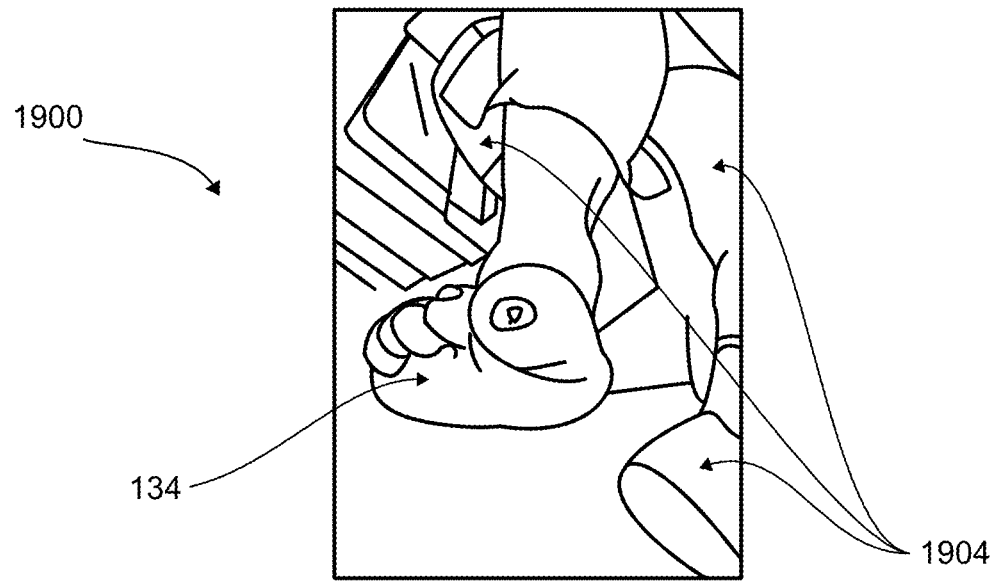
FIG. 19 is a third problematic image.

Referring now to FIG. 19, therein is shown a third problematic image 1900. The third problematic image 1900 can be understood as problematic due to background clutter 1904, and the overly close distance between the body part 134 and the image-capturing device 110 of FIG. 1.

Further, the size of the body part 134, due to the body part 134 being close to the camera, is larger than the image of FIG. 17 and should be moved further from the image-capturing device 110 in order to ensure the body part 134 is a similar size to the body part 134 captured in the related images.

Yet further, the pose of the body part 134 can be considered to be improperly aligned as the leg line aligns with right side of foot rather than the center, which is where previous images captured the leg line.

Figure 20:
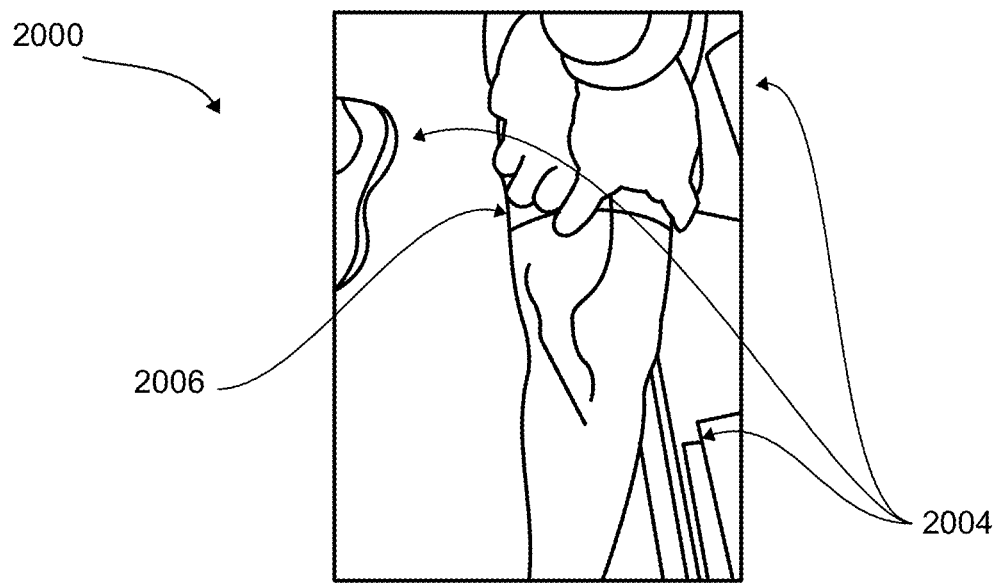
FIG. 20 is a fourth problematic image.

Referring now to FIG. 20, therein is shown a fourth problematic image 2000. The fourth problematic image 2000 can be understood as problematic due to background clutter 2004, hands in the image that do not correspond to the region-of-interest 138 of FIG. 1, shallow lighting, shade from the hands 2006, and uneven focus.

The image system 100 can generate instructions to clear the background clutter, remove the extraneous body parts 134, increase lighting intensity, and change focus.

Figure 21:
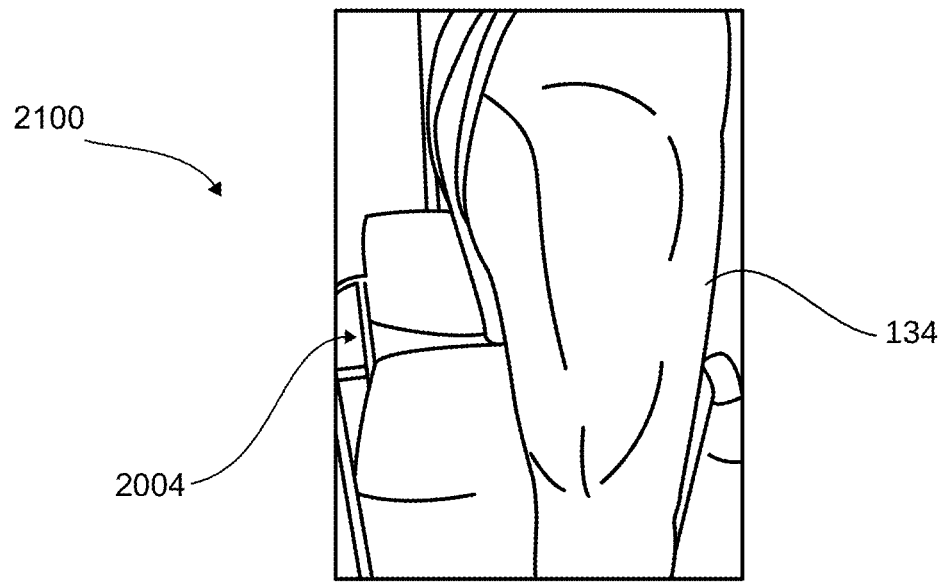
FIG. 21 is a fifth problematic image.

Referring now to FIG. 21, therein is shown a fifth problematic image 2100. The fifth problematic image 2100 can be understood as problematic due to background clutter 2104, extremely shallow lighting, and uneven focus.

The image system 100 can generate instructions to clear the background clutter, increase lighting intensity, and change focus.

Figure 22:
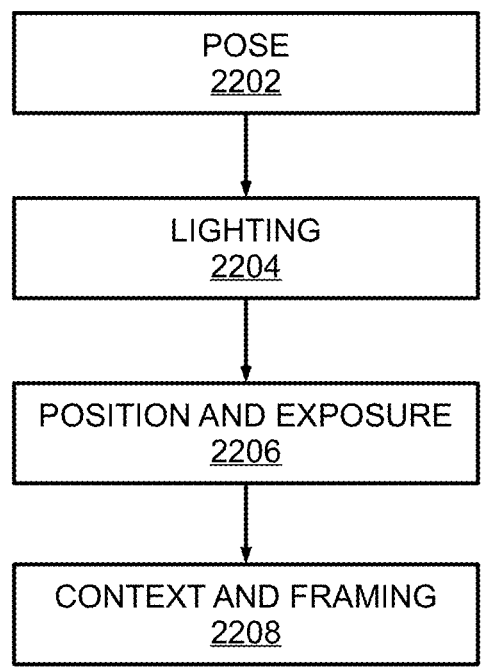
FIG. 22 is a control flow for the image system.

Referring now to FIG. 22, therein is shown a control flow for the image system 100. It has been discovered, for example, that for a series of the subsequent images 128 of FIG. 1 to properly represent progress and healing of an ailment, it is important that the imaging parameters, used in obtaining the original image 120 of FIG. 1, be substantially similar to imaging parameters used for obtaining the subsequent images 124.

When the imaging parameters of the original image 120 and the subsequent images 128 are substantially similar, information can be extracted from the original image 120 and the subsequent images 128, for computing and tracking of quantitative progress (or even regress) of the subject 122 of FIG. 1.

As an illustrative example, the control flow can include a pose step 2202, a lighting step 2204, a position and exposure step 2206, and a context and framing step 2208. It is contemplated that this can help to provide a consistency of pose, consistency and quality of lighting, consistency of camera position and camera exposure, image context, and proper framing which can include the definition of the region-of-interest 138 of FIG. 1.

The image system 100 can be initiated by executing the pose step 2202. During the pose step 2202 original image 120 and the subsequent images 128 should be free of distracting and irrelevant body parts of the subject 122.

That is, no other body parts of the subject 122, such as hands, feet and legs, that are not afflicted with a medical condition of interest should not be in the scene or the frame of the original image 120 or the subsequent images 128. It is contemplated that when more than one part is afflicted with a condition requiring the use of the image system 100 to build the image history 132 of FIG. 1 comprising the original image 120 and the subsequent images 128, then each body part of the subject 122 should be separately prescribed by a doctor and each body part of the subject 122 should be photographed separately in order to build a unique image history for each body part.

The pose step 2202 can include removing the extraneous objects 1802 from the image frame 136 of FIG. 1. Removing the extraneous objects from the image frame 136 can provide a clean background free of furniture, clothing, irrelevant body parts, pets, and the like. Further it is contemplated that the background 126 of FIG. 1 should contrast well with skin of the body part 134 of FIG. 1.

For example, it has been discovered that beige, yellow, brown, and pink do not contrast well with the skin of the body part 134 and should be avoided in the background 126. The alignment of the body part 134 of the subject 122 within the subsequent image 128 at time t1 should align well with the original image 120 at time t0.

In order to achieve proper alignment, the background 126 image can be used as an overlay for alignment purposes. The subject 122 can align his body part 134 with the reverse of the background 126 ensuring proper alignment between the original image 120 and the subsequent images 128.

The image system 100 can further execute the lighting step 2204. It is contemplated that during the lighting step 2204, the lighting from the image history 132, including the original image 120 and the subsequent images 128 should be the same.

It has been discovered that in most cases, the best lighting can be soft and uniform without harsh shadows. During the lighting step 2204, lighting that has a color bias is avoided.

This includes the use of yellowish, greenish, and bluish light casts. This also includes mixed source lighting such as sunlight and incandescent light.

It has been discovered that older style fluorescent lights give a greenish light that may be unacceptable for collecting a proper image. However, newer florescent lights provide light without the greenish hue and can be effectively used.

It is contemplated that the background 126 or the full image can be analyzed for color during the lighting step 2204 to ensure that the lighting is appropriate. If the lighting in the image frame 136 contains lighting falling outside of thresholds, such as color thresholds or a variance threshold, which can be based on the original image 120 and the subsequent images 128. Feedback can be generated and displayed to the user. The feedback can include audio or text indicating that the lighting within the image frame 136 is not in compliance or is at variance with the rest of the images within the image history 132 including the original image 120.

Illustratively, the feedback could indicate that the incandescent lights are "too yellow" or the florescent lights are "too green". Yet further, during the lighting step 2204, the lighting brightness can be monitored from within the image-capturing device 110 of FIG. 1 for the image being acquired.

Lighting should not only be non-color biased but should also be bright enough to ensure a good shutter speed. Slow shutters under dim lighting can lead to hand shaking of camera, or motion of body part.

If the lighting is too low, falling below a lighting threshold or requiring a shutter speed falling below a shutter speed threshold, the image system 100 can generate and provide feedback that the "light level is too low". Alternatively, it is contemplated that in order to prevent images being taken at low lighting, an exposure integrity program can prevent taking photos when low lighting is detected.

It is contemplated that the exposure integrity program can be a set of thresholds on imaging parameters. It will be appreciated that if an imaging parameter is detected and falls outside one or more thresholds, then acquisition of an image can be blocked.

The exposure integrity program can operate during, or be comprised of steps or operations within, the lighting step 2204 and the position and exposure step 2206; as discussed, for example, with regard to FIG. 23. Specifically, some imaging parameters have lower and upper thresholds, other imaging parameters have only one threshold.

During the position and exposure step 2206 the background 126 can be overlaid on the subsequent image 128 being captured by the image-capturing device 110. It has been discovered that overlaying the background 126 can partially ensure a repeatable pose of the subject 122 throughout the image history 132. As will be appreciated, the distance of the camera to the body part 134 needs to be the same between images, and the tilt and role angles which together comprise the orientation of the camera need to be the same between images.

The tilt, pan, yaw, and the distance of the image-capturing devices 110 to the body part 134 can be monitored by the image-capturing device 110 during the position and exposure step 2206. Feed back in the form of instructions for aligning the image-capturing device 110 can be displayed for the user to properly align the image-capturing device 110 for proper alignment between images within the image history 132.

Illustratively, it is contemplated that feedback in the way of instructions include distance instructions including: "move closer" or "move further away from body part".

Further, the instructions can include instructions to change the angle of the image-capturing device 110 by providing curved arrows indicating which direction the image-capturing device 110 should be rotated in order to match the position of the image-capturing device 110 with respect to the body part 134 for earlier images in the image history 132 including the original image 120.

It is contemplated, in some embodiments, that the exposure or image capture, can be withheld until the image-capturing device 110 is at the proper distance and position relative to the body part 134 being photographed. It has been discovered that the subsequent images 128 having imaging parameters within thresholds in relation to the original image 120 enables consistent repeatable images to be acquired. As will be appreciated, having consistent repeatable images can provide numerous advantages including lower barriers to entry, greater effectiveness of treatment, and intuitive control of the image system 100.

Further, ensuring consistent images can include defining the background 126 as an active overlay on the servers 104 of FIG. 1. The background 126 can be downloaded as an active overlay each time one of the subsequent images 128 is captured.

Yet further, each time one of the subsequent images 128 are captured, the imaging parameters can be checked to ensure consistency with the image history 132 and the original image 120. Illustratively, when the scene of the subsequent image 128 is too dark, this can be detected when the exposure time or the ISO speed cannot be adjusted automatically by the image-capturing device 110 to be within the thresholds for these imaging parameters. When this occurs, feedback can be generated and displayed as: "Use brighter lighting".

When harsh shadows are detected by current light/dark markers or with a histogram algorithm, the image system 100 can generate the feedback: "Use more diffuse lighting". When the camera position does not match with the camera position used for the original image 120, the image system 100 can generate arrows to define the rotation needed to bring the image-capturing device 110 into compliance with the camera position first used for the original image 120. The arrows providing feedback for the position of angular position of the image-capturing device 110 can also include distance arrows indicating that a change is needed to correct for an improper focus distance.

It is contemplated that when all conditions are met, the image system 100 can automatically capture the subsequent image 128. The context and framing step 2208 can be initiated to ensure that the body part 134 is properly positioned within the image frame 136 with the region-of-interest 138 clearly visible and consistent with the display of the region-of-interest 138 in other images contained within the image history 132.

During the context and framing step 2208, it is contemplated that an overlay test could be used to ensure proper matching of the body part 134 of the subject 122 within the image frame between the original image 120 and the image currently displayed on the user device 108. The overlay test is contemplated to include matching a computed overlay, such as the background 126 for the original image 120, to skin area detected within the subsequent image 128.

If the overlay generated based on the original image 120 does not match the subsequent image 128 displayed on the user device 108, the current exposure will be blocked and the subsequent image 128 not captured. The overlay test can evaluate the subsequent image 128 displayed on the user device 108 to the overlay based on the original image 120 sector by sector. In other words, the overlay test can evaluate each quarter of the subsequent image 128 displayed on the user device 108 including mid-to-mid and corner-to-corner.

Referring now to FIG. 23, therein is shown a control flow for the image system 100. It is contemplated that the control flow can be implemented as a series of process steps.

The process steps may be instructions stored on a non-transitory computer-readable medium, that when executed by a processor, perform the process steps. Those of ordinary skill in the art will recognize that the steps can be performed in any order —except where order is required by the context or elements of an individual step—steps may be broken into multiple smaller steps or contained into fewer larger steps without deviating from the skin color system as disclosed herein.

It has been discovered, for example, that for a series of the subsequent images 128 of FIG. 1 to properly represent progress and healing of an ailment, it is important that imaging parameters 2302, used in obtaining the original image 120 of FIG. 1, be substantially similar to imaging parameters used for obtaining the subsequent images 124.

When the imaging parameters of the original image 120 and the subsequent images 128 are substantially similar, information can be extracted from the original image 120 and the subsequent images 128, for computing and tracking of quantitative progress (or even regress) of the subject 122 of FIG. 1.

It has further been discovered that the careful control, monitoring, and use of imaging parameters 2302 when evaluated against thresholds, can enable the image system 100 of FIG. 1 to take the subsequent images 128 with exceptionally similar imaging parameters 2302 between the subsequent images 128 and the original image 120. This allows the image system 100 to capture unexpectedly higher quality images while using the thresholds, which are not employed by any known manual imaging process.

Illustratively, for example, the control flow of FIG. 23 can include multiple steps contemplated to be performed during the lighting step 2204 of FIG. 22 or during the position and exposure step 2206 of FIG. 22. It is contemplated that the lighting step 2204, the position and exposure step 2206, or a combination thereof can begin with an image detection step 2302 where the image-capturing device 110 of FIG. 1 is turned on and allowed to begin detecting an image, such as the subsequent image 128 or the original image 120.

The image detection step 2302 can further collect information from other sensors contained within the image-capturing device 110 such as directional data from magnetometers, or acceleration and movement data from gyroscopes and accelerometers. The information collected from the image-capturing device 110 during the image detection step 2302 can be used by a skin determination step 2304, a tilt step 2306, a pan step 2308, a yaw step 2310, a focal distance step 2312, an exposure time step 2314, an ISO step 2316, a positioning step 2318, a shake step 2320, and a focus step 2322, in order to generate the imaging parameters 2302.

It has been discovered that the amount of skin of the subject 122 within the image frame can be important when the image system 100 is implemented in medical settings, for example. This results from the region-of-interest 138 being largely contained on and within the skin of the subject 122.

The skin determination step 2304 can be executed by the image system 100. The skin determination step 2304 can determine the amount of skin within the frame of the subsequent image 128 utilizing the YCrCb skin selection of FIG. 4 or the RGB skin selection of FIG. 5.

The skin determination step 2304 can evaluate the information output from the image detection step 2302, such as the subsequent image 128 for example, and can output the amount of area within the subsequent image 128 occupied by skin of the subject 122. The image system 100 can evaluate the result of the skin determination step 2304 with respect to a lower skin threshold 2324. The lower skin threshold 2324 can be set to half of the area of the subsequent image 128, to a percentage of the skin area detected within the original image 120, or a combination thereof.

In other contemplated embodiments, it is contemplated that the skin threshold can also include an upper skin threshold and a relational threshold which would operate against previous images rather than the image in general.

That is if the skin threshold 2324 on the upper limit was sixty percent the relational threshold could be plus or minus one percent from the previous image. Continuing with this example, the skin threshold 2324 would be between fifty and sixty percent while the relational threshold might be forty-five to fifty-five percent based on a previous image having fifty percent coverage.

The result of the skin determination step 2304 can be evaluated against the lower skin threshold 2324 within a skin determination step 2326. The skin determination step 2326 can initiate the execution of a feedback step 2328 based on the amount of skin of the subject 122, within the frame of the subsequent image 128, being below the lower skin threshold 2324.

The feedback step 2328 can provide instructions to increase the size of the region-of-interest 138 displayed within the subsequent image 128 using visual, audio, or haptic feedback. For example, text can be displayed to move closer or further. Also, the feedback could include the use of directional arrows for directing the image-capturing device 110 closer or further from the subject 122.

Once the image system 100 has executed the feedback step 2328, the image system 100 can again execute the image detection step 2302 where the subsequent image 128 can be re-evaluated with the skin determination step 2304 and the skin determination step 2326 for compliance with the lower skin threshold 2324.

The skin determination step 2326 can allow capture and recording of the subsequent image 128 within an allow capture step 2330, based on the amount of skin of the subject 122, within the frame of the subsequent image 128, being above the lower skin threshold 2324. Once capture of the subsequent image 128 has been allowed within the allow capture step 2330, the subsequent image 128 can be stored in the image history 132 of FIG. 1 uniquely generated for an individual body part of the subject 122 contained within the subsequent image 128.

It has been discovered that ensuring a consistent tilt 112 of FIG. 1 between the image-capturing device 110 and the subject 122 during the original image 120 and the subsequent image 128 is important for maintaining consistency among images for proper analysis. This is due to the angle of the subject 122 portrayed within the image frame changing based on a changing tilt 112 of the image-capturing device 110, which would make calculation, evaluation, and comparison of difficult.

The tilt step 2306 can be executed by the image system 100. The tilt step 2306 can determine the tilt 112, that is, whether the image-capturing device 110 is tilted with respect to a horizontal plane. When executing the tilt step 2306, the image-capturing device 110 can provide accurate inclination sensing utilizing accelerometers including inclination sensing using a gravity vector on the accelerometer to determine the tilt angle.

The tilt step 2306 can evaluate the information output from the image detection step 2302 such as the subsequent image 128 along with additional sensor data including from accelerometers and gyroscopes, for example, and can output a tilt angle relative to a horizontal plane. The image system 100 can evaluate the result of the tilt step 2306 with respect to a tilt threshold 2334. The tilt threshold 2334 can be an upper and lower threshold.

The upper threshold can be a percentage or fixed amount above the tilt angle of the image-capturing device 110 during the capture of the original image 120 and lower threshold can be a percentage or fixed amount below the tilt angle of the image-capturing device 110 during the capture of the original image 120.

The result of the tilt step 2306 can be evaluated against the upper and lower tilt thresholds 2334 within a tilt determination step 2336. The tilt determination step 2336 can initiate the execution of the feedback step 2328 based on the tilt angle of the image-capturing device 110, being below the lower tilt threshold or above the upper tilt threshold.

The feedback step 2328 can provide instructions to rotate the image-capturing device 110 up or down relative to the horizontal plane using visual, audio, or haptic feedback. For example, text can be displayed to tilt up or down. Also, the feedback could include the use of directional arrows for directing the image-capturing device 110 to tilt.

Once the image system 100 has executed the feedback step 2328, the image system 100 can again execute the image detection step 2302 where the subsequent image 128 can be re-evaluated with the tilt step 2306 and the tilt determination step 2336 for compliance with the tilt threshold 2334.

The tilt determination step 2336 can initiate the capture and recording of the subsequent image 128 by initiating the execution of the allow capture step 2330, based on the tilt angle of the image-capturing device 110, being within the upper and lower tilt thresholds 2334. Once capture of the subsequent image 128 has been allowed within the allow capture step 2330, the subsequent image 128 can be stored in the image history 132 uniquely generated for the individual body part of the subject 122 contained within the subsequent image 128.

It has been discovered that ensuring a consistent pan 114 of FIG. 1 of the image-capturing device 110 during the original image 120 and the subsequent image 128 can be important for maintaining consistency among images for proper analysis. This is due to the angle of the subject 122 or lighting possibly changing based on a changing pan 114 of the image-capturing device 110, which would make calculation, evaluation, and comparison of difficult.

The pan step 2308 can be executed by the image system 100. The pan step 2308 can determine the pan 114, that is, whether the image-capturing device 110 is paned with respect to north. When executing the pan step 2308, the image-capturing device 110 can provide a pan angle utilizing accelerometers and magnetometers.

The pan step 2308 can evaluate the information output from the image detection step 2302 such as the subsequent image 128 along with additional sensor data including from magnetometers, accelerometers, and gyroscopes, for example, and can output a pan angle as a directional output relative to north. The image system 100 can evaluate the result of the pan step 2308 with respect to a pan threshold 2338. The pan threshold 2338 can be an upper and lower threshold.

The upper threshold can be a percentage or fixed amount above the pan angle of the image-capturing device 110 during the capture of the original image 120 and lower threshold can be a percentage or fixed amount below the pan angle of the image-capturing device 110 during the capture of the original image 120.

The result of the pan step 2308 can be evaluated against the upper and lower pan thresholds 2340 within a pan determination step 2340. The pan determination step 2340 can initiate the execution of the feedback step 2328 based on the pan angle of the image-capturing device 110, being below the lower pan threshold or above the upper pan threshold.

The feedback step 2328 can provide instructions to rotate the image-capturing device 110 left or right within the horizontal plane using visual, audio, or haptic feedback. For example, text can be displayed to pan left or right. Also, the feedback could include the use of directional arrows for directing the image-capturing device 110 to pan.

Once the image system 100 has executed the feedback step 2328, the image system 100 can again execute the image detection step 2302 where the subsequent image 128 can be re-evaluated with the pan step 2308 and the pan determination step 2340 for compliance with the pan threshold 2338.

The pan determination step 2340 can initiate the capture and recording of the subsequent image 128 by initiating the execution of the allow capture step 2330, based on the pan angle of the image-capturing device 110, being within the upper and lower pan thresholds 2338. Once capture of the subsequent image 128 has been allowed within the allow capture step 2330, the subsequent image 128 can be stored in the image history 132 uniquely generated for the individual body part of the subject 122 contained within the subsequent image 128.

It has been discovered that ensuring a consistent yaw 116 of FIG. 1 between the image-capturing device 110 and the subject 122 during the original image 120 and the subsequent image 128 is important for maintaining consistency among images for proper analysis. This is due to the angle of the subject 122 portrayed within the image frame changing based on a changing yaw 116 of the image-capturing device 110, which would make calculation, evaluation, and comparison of difficult.

The yaw step 2310 can be executed by the image system 100. The yaw step 2310 can determine the yaw 116, that is, whether the image-capturing device 110 is angled with respect to vertical. When executing the yaw step 2310, the image-capturing device 110 can provide a yaw angle utilizing accelerometers.

The yaw step 2310 can evaluate the information output from the image detection step 2302 such as the subsequent image 128 along with additional sensor data including from accelerometers and gyroscopes, for example, and can output a yaw angle as an angular direction relative to horizontal. The image system 100 can evaluate the result of the yaw step 2310 with respect to a yaw threshold 2342. The yaw threshold 2342 can be an upper and lower threshold.

The upper threshold can be a percentage or fixed amount above the yaw angle of the image-capturing device 110 during the capture of the original image 120 and lower threshold can be a percentage or fixed amount below the yaw angle of the image-capturing device 110 during the capture of the original image 120.

The result of the yaw step 2310 can be evaluated against the upper and lower yaw thresholds 2348 within a yaw determination step 2344. The yaw determination step 2344 can initiate the execution of the feedback step 2328 based on the yaw angle of the image-capturing device 110, being below the lower yaw threshold or above the upper yaw threshold.

The feedback step 2328 can provide instructions to rotate the image-capturing device 110 using visual, audio, or haptic feedback. For example, text can be displayed to yaw to one side or the other. Also, the feedback could include the use of directional arrows for directing the image-capturing device 110 to yaw.

Once the image system 100 has executed the feedback step 2328, the image system 100 can again execute the image detection step 2302 where the subsequent image 128 can be re-evaluated with the yaw step 2310 and the yaw determination step 2344 for compliance with the yaw threshold 2342.

The yaw determination step 2344 can initiate the capture and recording of the subsequent image 128 by initiating the execution of the allow capture step 2330, based on the yaw angle of the image-capturing device 110, being within the upper and lower yaw thresholds 2344. Once capture of the subsequent image 128 has been allowed within the allow capture step 2330, the subsequent image 128 can be stored in the image history 132 uniquely generated for the individual body part of the subject 122 contained within the subsequent image 128.

It has been discovered that ensuring a consistent distance 118 of FIG. 1 between the image-capturing device 110 and the subject 122 during the original image 120 and the subsequent image 128 is important for maintaining consistency among images for proper analysis. This is due to the size of the subject 122 changing with a change in distance making calculation, evaluation, and comparison of wound size difficult.

The focal distance step 2312 can be executed by the image system 100. The focal distance step 2312 can determine the distance 118 between the image-capturing device 110 and the subject 122. When executing the focal distance step 2312, the image-capturing device 110 can provide the distance utilizing the focal distance calculations of the image-capturing device 110 during the image detection step 2302.

The focal distance step 2312 can evaluate the information output from the image detection step 2302 such as the focal distance of the subsequent image 128, for example, and can output a distance relative to the subject 122. The image system 100 can evaluate the result of the focal distance step 2312 with respect to a distance threshold 2346. The distance threshold 2346 can be an upper and lower threshold.

The upper threshold can be a percentage or fixed amount above the distance between the image-capturing device 110 and the subject 122 during the capture of the original image 120 and lower threshold can be a percentage or fixed amount below the distance between the image-capturing device 110 and the subject 122 during the capture of the original image 120. The distance threshold 2346 should have a minimum value higher than a minimum focal distance for the image-capturing device 110.

The result of the focal distance step 2312 can be evaluated against the upper and lower distance thresholds 2346 within a distance determination step 2348. The distance determination step 2348 can initiate the execution of the feedback step 2328 based on the distance between the image-capturing device 110 and the subject 122, being below the lower distance threshold or above the upper distance threshold.

The feedback step 2328 can provide instructions to rotate the image-capturing device 110 using visual, audio, or haptic feedback. For example, text can be displayed to move closer or further. Also, the feedback could include the use of directional arrows for directing the image-capturing device 110 closer or further from the subject 122.

Once the image system 100 has executed the feedback step 2328, the image system 100 can again execute the image detection step 2302 where the subsequent image 128 can be re-evaluated with the focal distance step 2312 and the distance determination step 2348 for compliance with the distance threshold 2346.

The distance determination step 2348 can initiate the capture and recording of the subsequent image 128 by initiating the execution of the allow capture step 2330, based on the distance 118 between the image-capturing device 110 and the subject 122, being within the upper and lower distance thresholds 2346. Once capture of the subsequent image 128 has been allowed within the allow capture step 2330, the subsequent image 128 can be stored in the image history 132 uniquely generated for the individual body part of the subject 122 contained within the subsequent image 128.

It has been discovered that ensuring a consistent exposure time during the original image 120 and the subsequent image 128 is important for maintaining consistency among images for proper analysis. This is due to the lighting and blur changing based on differing exposure times of the image-capturing device 110, which would make calculation, evaluation, and comparison of difficult.

The exposure time step 2314 can be executed by the image system 100. The exposure time step 2314 can determine the exposure time which can result in, and from, many imaging properties.

Illustratively for example, if the exposure time is too low, this can indicate low lighting. When executing the exposure time step 2314, the image-capturing device 110 can extract the exposure time determined by the image-capturing device 110 during the image detection step 2302. The image system 100 can evaluate the result of the exposure time step 2314 with respect to an exposure time threshold 2350. The exposure time threshold 2350 can be an upper threshold for preventing blur and ensuring the image-capturing device 110 is within a shake-proof range.

The exposure time threshold 2350 can be determined by the ability of a user to hold the image-capturing device 110 still. In some implementations, the image-capturing device 110 might have a form of stabilization, in such situations, the exposure time upper threshold can be longer.

Another factor determining the exposure time threshold 2350 can include the motion of the subject 122. In general, people can hold still for a limited time; the elderly and those with neurological disorders, however, may require fast exposures to prevent blur.

The upper threshold can be a percentage or fixed amount above the exposure time used by the image-capturing device 110 during the capture of the original image 120. The upper threshold can also be a fixed absolute exposure time such as $\frac{1}{50}$ to $\frac{1}{30}$ of a second.

Some image-capturing devices 110 may have vibration elimination features, however this only ensures that the camera does not shake during capture and has no impact on shaking of the region-of-interest 138 on the subject 122 under investigation. Illustratively, for example, exposure times longer than $\frac{1}{50}$ to $\frac{1}{30}$ sec can be rejected and used to generate a low light level warning for display on the image-capturing device 110.

The result of the exposure time step 2314 can be evaluated against the upper exposure time threshold 2352 within an exposure time determination step 2352. The exposure time determination step 2352 can initiate the execution of the feedback step 2328 based on the exposure time being above the upper exposure time threshold.

The feedback step 2328 can provide instructions to increase lighting using visual, audio, or haptic feedback. For example, text can be displayed to use better lighting. Also, the feedback could include the use of directional arrows or illumination icons for directing better lighting.

Once the image system 100 has executed the feedback step 2328, the image system 100 can again execute the image detection step 2302 where the subsequent image 128 can be re-evaluated with the exposure time step 2314 and the exposure time determination step 2352 for compliance with the exposure time threshold 2350.

Alternatively, when harsh shadows are detected by light/dark markers or with a histogram algorithm on the subsequent image 128, the image system 100 can generate the warning: "Use more diffuse lighting".

The exposure time determination step 2352 can initiate the capture and recording of the subsequent image 128 by initiating the execution of the allow capture step 2330, based on the exposure time being below the upper exposure time threshold 2350. Once capture of the subsequent image 128 has been allowed within the allow capture step 2330, the subsequent image 128 can be stored in the image history 132 uniquely generated for the individual body part of the subject 122 contained within the subsequent image 128.

It has been discovered that ensuring a consistent ISO setting during the original image 120 and the subsequent image 128 is important for maintaining consistency among images for proper analysis. This is due to noise within the images changing based on differing ISO settings of the image-capturing device 110, which would make calculation, evaluation, and comparison of difficult.

The ISO step 2316 can be executed by the image system 100. The ISO step 2316 can determine the digital equivalent ISO or exposure index. Specifically, the ISO setting can be an exposure index rating, for example determined by the International Organization for Standardization (ISO), including Recommended Exposure Index (REI), Standard Output Sensitivity (SOS), a saturation-based technique, or one of two noise-based techniques.

It has been discovered, for example, that if the ISO is too high unacceptable amounts of noise can result. When executing the ISO step 2316, the image-capturing device 110 can extract the ISO setting determined by the image-capturing device 110 during the image detection step 2302. The image system 100 can evaluate the result of the ISO step 2316 with respect to an ISO threshold 2354. The ISO threshold 2354 can be an upper threshold.

It is contemplated that the sensor of the image-capturing device 110 can be examined by the image system 100 to determine the proper ISO setting. The image-capturing device 110 can provide warnings to the user if the ISO setting falls outside of ISO threshold 2354 or if the ISO setting of the original image 120 is incompatible with the ISO setting of the image-capturing device 110 for the subsequent image 128.

The upper threshold can be a percentage or fixed amount above the ISO setting used by the image-capturing device 110 during the capture of the original image 120. The upper threshold can also be a fixed absolute ISO setting such as an ISO value of between 300 to 600 of a second.

When the ISO setting is too high, noisy or grainy images can result. To reduce the exposure time, the ISO setting can be increased; however, if the ISO setting is above the ISO threshold 2354, the benefits of the reduced exposure time can be ineffective resulting in unclear images.

The result of the ISO step 2316 can be evaluated against the upper ISO threshold 2356 within an ISO determination step 2356. The ISO determination step 2356 can initiate the execution of the feedback step 2328 based on the ISO being above the upper ISO threshold.

The feedback step 2328 can provide instructions to decrease ISO setting or increase lighting using visual, audio, or haptic feedback. For example, text can be displayed to use better lighting. Also, the feedback could include the use of directional arrows or illumination icons for directing the use of better lighting during image capture.

Once the image system 100 has executed the feedback step 2328, the image system 100 can again execute the image detection step 2302 where the subsequent image 128 can be re-evaluated with the ISO step 2316 and the ISO determination step 2356 for compliance with the ISO threshold 2354.

The ISO determination step 2356 can initiate the capture and recording of the subsequent image 128 by initiating the execution of the allow capture step 2330, based on the ISO being below the upper ISO threshold 2354. Once capture of the subsequent image 128 has been allowed within the allow capture step 2330, the subsequent image 128 can be stored in the image history 132 uniquely generated for the individual body part of the subject 122 contained within the subsequent image 128.

It has been discovered that ensuring a consistent position of the subject 122 within the original image 120 and the subsequent image 128 is important for maintaining consistency among images for proper analysis. This is due to the viewing angle and area of the region-of-interest 138 changing based on differing alignment of the image-capturing device 110, which would make calculation, evaluation, and comparison of difficult.

The positioning step 2318 can be executed by the image system 100. The positioning step 2318 can evaluate the output of the skin determination step 2304 with the background 126 of FIG. 1. The positioning step 2318 can determine how much of the skin detected within the skin determination step 2304 falls within the background 126 and how much falls within the skin capture area 702 of FIG. 7.

When executing the positioning step 2318, the image-capturing device 110 can determine how much of the skin of the subsequent image 128, detected within the skin determination step 2304, is contained within the background 126. The image system 100 can evaluate the result of the positioning step 2318 with respect to a position threshold 2358. The position threshold 2358 can be an upper threshold.

The upper threshold can be a percentage or fixed amount of background area overlapped by the skin detected in the skin determination step 2304. The result of the positioning step 2318 can be evaluated against the upper position threshold 2360 within a position determination step 2360.

If the background 126 does not match the subsequent image 128 displayed on the user device 110, the current exposure will be blocked and the subsequent image 128 not captured. The overlaid background 126 can be evaluated with the user device 108 sector by sector. In other words, the position determination step 2360 can evaluate each quarter of the subsequent image 128 displayed on the user device 108 including mid-to-mid and corner-to-corner against the background 126.

The position determination step 2360 can initiate the execution of the feedback step 2328 based on the amount of background area overlapped by the skin detected in the skin determination step 2304 being above the upper position threshold.

The feedback step 2328 can provide instructions to move the image-capturing device 110 to better capture the subject 122. Illustratively, for example, the feedback could include an overlay of the background 126 onto the capture screen for the subsequent image 128. Further the feedback can be other visual, audio, or haptic feedback. Once the image system 100 has executed the feedback step 2328, the image system 100 can again execute the image detection step 2302 where the subsequent image 128 can be re-evaluated with the positioning step 2318 and the position determination step 2360 for compliance with the position threshold 2358.

The position determination step 2360 can initiate the capture and recording of the subsequent image 128 by initiating the execution of the allow capture step 2330, based on the amount of background area overlapped by the skin detected in the skin determination step 2304 being below the upper position threshold 2358. Once capture of the subsequent image 128 has been allowed within the allow capture step 2330, the subsequent image 128 can be stored in the image history 132 uniquely generated for the individual body part of the subject 122 contained within the subsequent image 128.

It has been discovered that ensuring a stable capture of the original image 120 and the subsequent image 128 is important for maintaining consistency among images for proper analysis. This is due to the blurring of the subject 122 when the image-capturing device 110 is shaken, which would make calculation, evaluation, and comparison of difficult.

The shake step 2320 can be executed by the image system 100. The shake step 2320 can evaluate the information output from the image detection step 2302 such as the subsequent image 128 along with additional sensor data including from accelerometers and gyroscopes, for example, and can output a movement amount or an acceleration indicative of shake.

The image system 100 can evaluate the result of the shake step 2320 with respect to a shake threshold 2362. The shake threshold 2362 can be an upper threshold.

The upper threshold can be a percentage or fixed amount of motion or acceleration. The result of the shake step 2320 can be evaluated against the upper shake threshold 2364 within a shake determination step 2364. The shake determination step 2364 can initiate the execution of the feedback step 2328 based on the amount of acceleration or movement being above the upper shake threshold.

The feedback step 2328 can provide instructions to steady or mount the image-capturing device 110 to better capture the subject 122. Further the feedback can be other visual, audio, or haptic feedback. For example, text can be displayed to steady the image-capturing device 110. Also, the feedback could include the use of icons for directing the stabilization of the image-capturing device 110.

Once the image system 100 has executed the feedback step 2328, the image system 100 can again execute the image detection step 2302 where the subsequent image 128 can be re-evaluated with the shake step 2320 and the shake determination step 2364 for compliance with the shake threshold 2362.

The shake determination step 2364 can initiate the capture and recording of the subsequent image 128 by initiating the execution of the allow capture step 2330, based on the amount acceleration or motion detected, being below the upper shake threshold 2362. Once capture of the subsequent image 128 has been allowed within the allow capture step 2330, the subsequent image 128 can be stored in the image history 132 uniquely generated for the individual body part of the subject 122 contained within the subsequent image 128.

It has been discovered that ensuring a consistent focus of the subject 122 within the original image 120 and the subsequent image 128 is important for maintaining consistency among images for proper analysis. This is due to unfocused features of the region-of-interest 138 being difficult to calculate, evaluate and compare.

The focus step 2322 can be executed by the image system 100. The focus step 2322 can evaluate the information output from the image detection step 2302 such as the subsequent image 128 along with information regarding the optics of the image-capturing device 110, for example, and can output a focus of the region-of-interest 138 of FIG. 1.

The focus can be computed by the image-capturing device 110 utilizing phase detection or contrast detection, for example. The image system 100 can evaluate the result of the focus step 2322 with respect to a focus threshold 2366. The focus threshold 2366 can be an upper threshold.

The upper threshold can simply be whether the region-of-interest 138 is in focus. The result of the focus step 2322 can be evaluated against the upper focus threshold 2368 within a focus determination step 2368. The focus determination step 2368 can initiate the execution of the feedback step 2328 based on the amount of acceleration or movement being above the upper focus threshold.

The feedback step 2328 can provide instructions to focus the image-capturing device 110 on the region-of-interest 138. Further the feedback can be other visual, audio, or haptic feedback. Once the image system 100 has executed the feedback step 2328, the image system 100 can again execute the image detection step 2302 where the subsequent image 128 can be re-evaluated with the focus step 2322 and the focus determination step 2368 for compliance with the focus threshold 2366.

The focus determination step 2368 can initiate the capture and recording of the subsequent image 128 by initiating the execution of the allow capture step 2330, based on whether the region-of-interest 138 is focused and therefore below the upper focus threshold 2366. Once capture of the subsequent image 128 has been allowed within the allow capture step 2330, the subsequent image 128 can be stored in the image history 132 uniquely generated for the individual body part of the subject 122 contained within the subsequent image 128.

Together with the subsequent images 128 stored in the image history 132, the image system 100 can also store the imaging parameters 2302 output from the skin determination step 2304, tilt step 2306, pan step 2308, yaw step 2310, focal distance step 2312, exposure time step 2314, ISO step 2316, positioning step 2318, shake step 2320, and the focus step 2322 as metadata of the original image 120 and the subsequent images 128.

It is contemplated that the allow capture step 2330 could be replaced with a capture step. For example, it is contemplated that when all conditions are met meaning the imaging parameters 2302 are all found to be within the thresholds, the image system 100 can automatically capture the subsequent image 128.

It has been unexpectedly discovered that ensuring the imaging parameters 2302 calculated for the original image 120 are substantially similar to the imaging parameters 2302 calculated for the subsequent images 128 greatly decreases computer processing overhead, computer storage overhead, and computer data communications overhead by ensuring that the image histories 132 contain only consistent useable images rather than a glut of useless images.

Further, ensuring consistency of imaging parameters 2302 between the original image 120 and the subsequent images 128, in the manner described by FIG. 23, is not known to be employed by any human operator and yet enables the image system 100 to capture known good images in a way not previously achievable by computer. Still further, ensuring consistency of imaging parameters 2302 between the original image 120 and the subsequent images 128, in the manner described by FIG. 23, enables enhanced image processing, which would not be possible without consistent images.

For the sake of brevity, clarity, and descriptive ease, each of the imaging parameters 2302 can be further evaluated against a relational threshold 2370 as described above. The relational threshold can be evaluated within a relational threshold decision step 2372.

That is, each of the imaging parameters 2302 resulting from the skin determination step 2304, the tilt step 2306, the pan step 2308, the yaw step 2310, the focal distance step 2312, the exposure time step 2314, the ISO step 2316, the positioning step 2318, the shake step 2320, and the focus step 2322 could be evaluated against an upper relational threshold, a lower relational threshold, or a combination thereof. The relational thresholds 2370 should be understood to be thresholds calculated based on the imaging parameters 2302 of a previous subsequent image 128, when the previous subsequent image 128 is within the same image history 132.

The relational thresholds 2370 should be understood as different from the thresholds 2304, which are calculated based on the imaging parameters 2302 of an original image 120 within the image history 132, or are alternatively absolute thresholds pre-selected based on general application across different image-capturing devices 110.

In some contemplated embodiments, the relational thresholds 2370 could replace, or be used instead of, the thresholds 2304 which are not based on previous imaging parameters 2302 of previous images. It is further contemplated that the color correction process of FIG. 6 could be executed once the image system 100 has captured the subsequent image 128 within the allow capture step 2330, for example.

It has been discovered that extracting the image parameters including: an image focal distance, an image tilt, an image yaw, an image pan, an image ISO speed, and an image exposure time prior to the capture of the subsequent image 128 reduces storage and processor overhead by ensuring consistent images are captured rather than a multiplicity of marginally useful images.

Providing feedback based on the image focal distance being outside a distance threshold, the tilt being outside a tilt threshold, the yaw being outside a yaw threshold, the pan being outside a pan threshold, the ISO setting an ISO threshold, the exposure time being outside an exposure time threshold, or a combination thereof ensures consistency between the original image 120 and the subsequent image 128, which can provide numerous advantages including lower barriers to entry, greater effectiveness of treatment, and intuitive control of the image system 100.

It has been discovered that the highly discriminating image quality system 100 can enable the back-end computing system to run more effectively since extra junk data and images do not need to be managed, stored, or transmitted. That is, when the image quality system 100 determines that an image should not be taken, the image quality system 100 runs faster requiring less processing, storage, energy, and data transmission overhead because junk data is excluded.

Thus, it has been discovered that the image system furnishes important and heretofore unknown and unavailable solutions, capabilities, and functional aspects. The resulting configurations are straightforward, cost-effective, uncomplicated, highly versatile, accurate, sensitive, and effective, and can be implemented by adapting known components for ready, efficient, and economical manufacturing, application, and utilization.

While the image system has been described in conjunction with a specific best mode, it is to be understood that many alternatives, modifications, and variations will be apparent to those skilled in the art in light of the preceding description. Accordingly, it is intended to embrace all such alternatives, modifications, and variations, which fall within the scope of the included claims. All matters set forth herein or shown in the accompanying drawings are to be interpreted in an illustrative and non-limiting sense.

As will be appreciated, the A method of operating an image integrity and repeatability system comprising: acquiring an original image; extracting a protocol focal distance from the original image, a protocol tilt from the original image, a protocol yaw from the original image, a protocol pan from the original image, a protocol ISO speed from the original image, and a protocol exposure time from the original image; recording the original image to an image history; determining an area within an image frame of the original image as a skin area; creating a background as the inverse of the skin area within the image frame of the original image; and acquiring a subsequent image including: extracting image parameters including an image focal distance, an image tilt, an image yaw, an image pan, an image ISO speed, and an image exposure time from the subsequent image, providing feedback based on the image focal distance being outside a distance threshold, the image tilt being outside a tilt threshold, the image yaw being outside a yaw threshold, the image pan being outside a pan threshold, the image ISO speed being outside an ISO threshold, the image exposure time being outside an exposure time threshold, or a combination thereof, prohibiting capture of the subsequent image based on one or more of the image parameters being outside the distance threshold, the tilt threshold, the yaw threshold, the pan threshold, the ISO threshold, the exposure time threshold, or a combination thereof, displaying the background overlaid on the subsequent image, and storing the subsequent image to the image history based on the image parameters of the subsequent image being within the distance threshold, the tilt threshold, the yaw threshold, the pan threshold, the ISO threshold, and the exposure time threshold, are to be considered functional controlling functional data which serves to control the operation of the image system 100 processing the data. These steps alone and in combination inherently comprise, or reflect, corresponding technical features of the device.

As will be appreciated, extracting a protocol focal distance from the original image, a protocol tilt from the original image, a protocol yaw from the original image, a protocol pan from the original image, a protocol ISO speed from the original image, and a protocol exposure time from the original image is not a process known to be used by human operators but instead is believed to be isolated to computer implemented image systems 100 and allows consistent capture of images, which has previously not been possible with an imaging system alone. Further It has been discovered that this extraction of data improves the functionality of the image system 100 by reducing the onerous processing, storage, and communications overhead which results from capturing images not consistent with the original image 120.

Further, determining an area within an image frame of the original image as a skin area; creating a background as the inverse of the skin area within the image frame of the original image; and acquiring a subsequent image including: extracting image parameters including an image focal distance, an image tilt, an image yaw, an image pan, an image ISO speed, and an image exposure time from the subsequent image, is not a process known to be used by human operators but instead is believed to be isolated to computer implemented image systems 100 image systems 100 and allows consistent capture of images, which has previously not been possible with an imaging system alone. Further It has been discovered that this determination, creation, and acquisition improves the functionality of the image system 100 by reducing the onerous processing, storage, and communications overhead which results from capturing multiple subsequent images 128 not consistent with the original image 120.

Yet further, providing feedback based on the image focal distance being outside a distance threshold, the image tilt being outside a tilt threshold, the image yaw being outside a yaw threshold, the image pan being outside a pan threshold, the image ISO speed being outside an ISO threshold, the image exposure time being outside an exposure time threshold, or a combination thereof, prohibiting capture of the subsequent image based on one or more of the image parameters being outside the distance threshold, the tilt threshold, the yaw threshold, the pan threshold, the ISO threshold, the exposure time threshold, or a combination thereof, and displaying the background overlaid on the subsequent image, is not a process known to be used by human operators but instead is believed to be isolated to computer implemented image systems 100 image systems 100 and allows consistent capture of images, which has previously not been possible with an imaging system alone. Further It has been discovered that providing the feedback step improves the functionality of the image system 100 by reducing the onerous processing, storage, and communications overhead which results from capturing images not consistent with the original image 120.

What is claimed is:

1. A method of operating an image integrity and repeatability system comprising:
   acquiring an original image;
   extracting a protocol focal distance from the original image, a protocol tilt from the original image, a protocol yaw from the original image, a protocol pan from the original image, a protocol ISO speed from the original image, and a protocol exposure time from the original image;
   recording the original image to an image history;
   determining an area within an image frame of the original image as a skin area;
   creating a background as an inverse of the skin area within the image frame of the original image; and
   acquiring a subsequent image including:
      extracting image parameters including an image focal distance, an image tilt, an image yaw, an image pan, an image ISO speed, and an image exposure time from the subsequent image,
      providing feedback based on the image focal distance being outside a distance threshold, the image tilt being outside a tilt threshold, the image yaw being outside a yaw threshold, the image pan being outside a pan threshold, the image ISO speed being outside an ISO threshold, the image exposure time being outside an exposure time threshold, or a combination thereof,
      prohibiting capture of the subsequent image based on one or more of the image parameters being outside the distance threshold, the tilt threshold, the yaw threshold, the pan threshold, the ISO threshold, the exposure time threshold, or a combination thereof,
      displaying the background overlaid on the subsequent image, and
      storing the subsequent image to the image history based on the image parameters of the subsequent image being within the distance threshold, the tilt threshold, the yaw threshold, the pan threshold, the ISO threshold, and the exposure time threshold.

2. The method of claim 1 wherein storing the subsequent image includes storing the subsequent image within the image history uniquely generated for an individual body part within the original image.

3. The method of claim 1 wherein acquiring the subsequent image further includes:
   extracting the image parameters including a subsequent image skin area from the subsequent image, and
   evaluating the subsequent image skin area against a position threshold sector by sector against the background.

4. The method of claim 1 further comprising acquiring a second subsequent image including evaluating a second subsequent image parameter against a relational threshold, the relational threshold based on one of the image parameters of the subsequent image.

5. The method of claim 1 further comprising detecting the definition of a region of interest within the image frame of the original image.

6. A non-transitory computer readable medium in useful association with a processor including instructions configured to:
   extract a protocol focal distance from an original image, a protocol tilt from the original image, a protocol yaw from the original image, a protocol pan from the original image, a protocol ISO speed from the original image, and a protocol exposure time from the original image;
   record the original image to an image history;
   determine an area within an image frame of the original image as a skin area;
   create a background as an inverse of the skin area within the image frame of the original image; and
   acquire a subsequent image including instructions configured to:
      extract image parameters including an image focal distance, an image tilt, an image yaw, an image pan, an image ISO speed, and an image exposure time from the subsequent image,
      provide feedback based on the image focal distance being outside a distance threshold, the image tilt being outside a tilt threshold, the image yaw being outside a yaw threshold, the image pan being outside a pan threshold, the image ISO speed being outside an ISO threshold, the image exposure time being outside an exposure time threshold, or a combination thereof,
      prohibit capture of the subsequent image based on one or more of the image parameters being outside the distance threshold, the tilt threshold, the yaw threshold, the pan threshold, the ISO threshold, the exposure time threshold, or a combination thereof, display the background overlaid on the subsequent image, and store the subsequent image to the image history based on the image parameters of the subsequent image being within the distance threshold, the tilt threshold, the yaw threshold, the pan threshold, the ISO threshold, and the exposure time threshold.

7. The instructions of claim 6 wherein the instructions configured to store the subsequent image further includes instructions configured to store the subsequent image within the image history uniquely generated for an individual body part within the original image.

8. The instructions of claim 6 wherein the instructions configured to acquire the subsequent image further includes instructions configured to:

extract the image parameters including a subsequent image skin area from the subsequent image, and evaluate the subsequent image skin area against a position threshold sector by sector against the background.

9. The instructions of claim 6 further includes instructions configured to acquire a second subsequent image including evaluating a second subsequent image parameter against a relational threshold, the relational threshold based on one of the image parameters of the subsequent image.

10. The instructions of claim 6 further includes instructions configured to detect the definition of a region of interest within the image frame of the original image.

* * * * *